(12) United States Patent
Khosravi-Far et al.

(10) Patent No.: US 11,541,393 B2
(45) Date of Patent: Jan. 3, 2023

(54) SYSTEMS, APPARATUS, AND METHODS FOR DETECTING PATHOGENS

(71) Applicant: InnoTech Precision Medicine, Inc., Boston, MA (US)

(72) Inventors: Roya Khosravi-Far, Boston, MA (US); Reza Mollaaghababa, Natick, MA (US)

(73) Assignee: INNOTECH PRECISION MEDICINE, INC., Boston, MA (US)

( * ) Notice: Subject to any disclaimer, the term of this patent is extended or adjusted under 35 U.S.C. 154(b) by 0 days.

(21) Appl. No.: 17/484,842

(22) Filed: Sep. 24, 2021

(65) Prior Publication Data
US 2022/0088584 A1 Mar. 24, 2022

Related U.S. Application Data

(60) Provisional application No. 63/082,694, filed on Sep. 24, 2020, provisional application No. 63/143,690, filed on Jan. 29, 2021.

(51) Int. Cl.
*B01L 3/00* (2006.01)
*B01L 7/00* (2006.01)

(52) U.S. Cl.
CPC .............. *B01L 3/508* (2013.01); *B01L 7/00* (2013.01); *B01L 2200/026* (2013.01); *B01L 2200/04* (2013.01); *B01L 2200/0689* (2013.01); *B01L 2200/10* (2013.01); *B01L 2200/16* (2013.01); *B01L 2300/044* (2013.01);
(Continued)

(58) Field of Classification Search
CPC ......... B01L 3/502715; B01L 3/502753; B01L 2300/0627; B01L 2300/0636; B01L 2300/0645; C12M 1/3407; C12Q 2563/116; C12Q 2565/607; C12Q 2563/119; C12Q 2563/125; C12Q 2563/131; G01N 27/414; G01N 27/4145
See application file for complete search history.

(56) References Cited

U.S. PATENT DOCUMENTS

| 2014/0302492 | A1 | 10/2014 | Blackburn et al. |
| 2018/0037952 | A1* | 2/2018 | Goldsmith ......... G01N 27/4145 |
| 2019/0284615 | A1* | 9/2019 | Fotouhi ............ G01N 33/56927 |

FOREIGN PATENT DOCUMENTS

| WO | 2009120183 A2 | 10/2009 |
| WO | 2015048173 A2 | 4/2015 |
| WO | 2017190139 A1 | 11/2017 |

OTHER PUBLICATIONS

Basha, I. H. K., et al, "Towards Multiplex Molecular Diagnosis—A Review of Microfluidic Genomics Technologies", Micromachines (Basel) 8, doi:10.3390/mi8090266 (2017).
(Continued)

*Primary Examiner* — Jill A Warden
*Assistant Examiner* — Dwayne K Handy
(74) *Attorney, Agent, or Firm* — McDermott Will & Emery LLP

(57) ABSTRACT

A sensor for detecting a target pathogen (e.g., a virus or a bacterium) in a specimen is disclosed, which includes at least two sensing units one of which is configured to detect at least one protein (such as a structural protein) associated with the target pathogen and another one is configured to detect at least one genetic component (e.g., an RNA or a DNA segment) associated with that pathogen (e.g., an RNA segment that is unique to that pathogen).

30 Claims, 28 Drawing Sheets

(52) U.S. Cl.
CPC ............... B01L 2300/0609 (2013.01); B01L 2300/0645 (2013.01); B01L 2300/0663 (2013.01); B01L 2300/12 (2013.01); B01L 2300/1822 (2013.01); B01L 2300/1894 (2013.01)

(56) References Cited

OTHER PUBLICATIONS

Chen, H., et al, "Point of care testing for infectious diseases", Clin Chim Acta 493, 138-147, doi:10.1016/j.cca.2019.03.008 (2019).
Chen, L., et al, "Performance of the Cobas(®) Influenza A/B Assay for Rapid Per-Based Detection of Influenza Compared to Prodesse ProFlu+ and Viral Culture", Eur J Microbiol Immunol (Bp) 5, 236-245, doi:10.1556/1886.2015.00046 (2015).
Ekrami, E. et al., "Potential Diagnostic Systems for Coronavirus Detection: a Critical Review", Biol Proced Online 22, 21, doi:10.1186/s12575-020-00134-4 (2020).
Giuffrida, M. C., et al., "Integration of isothermal amplification methods in microfluidic devices: Recent advances", Biosens Bioelectron 90, 174-186, doi:10.1016/j.bios.2016.11.045 (2017).
Hart, R. W. et al, "Point-of-care oral-based diagnostics", Oral Dis 17, 745-752, doi:10.1111/j.1601-0825.2011.01808.x (2011).
Huang, Y., et al, "Disease-Related Detection with Electrochemical Biosensors: A Review", Sensors (Basel) 17, doi:10.3390/s17102375 (2017).
Krokhine, S., et al, "Conventional and microfluidic methods for airborne virus isolation and detection", Colloids Surf B Biointerfaces 206, 111962, doi:10.1016/j.colsurfb.2021.111962 (2021).
Kwakye, S., et al, "Electrochemical microfluidic biosensor for nucleic acid detection with integrated minipotentiostat", Biosens Bioelectron 21, 2217-2223, doi:10.1016/j.bios.2005.11.017 (2006).
Mauk, M., et al., "Miniaturized devices for point of care molecular detection of HIV", Lab Chip 17, 382-394, doi:10.1039/c6lc01239f (2017).
Miocevic, O. et al, "Quantitative Lateral Flow Assays for Salivary Biomarker Assessment: A Review", Frontiers in Public Health 5, 133, doi:10.3389/fpubh.2017.00133 (2017).
Mohan, R. et al., "Clinical validation of integrated nucleic acid and protein detection on an electrochemical biosensor array for urinary tract infection diagnosis", PLoS One 6, e26846, doi:10.1371/journal.pone 0026846 (2011).
Niemz, A., et al., "Point-of-care nucleic acid testing for infectious diseases", Trends Biotechnol 29, 240-250, doi:10.1016/j.tibtech.2011.01.007 (2011).
Noah, N. M. et al, "Current Trends of Nanobiosensors for Point-of-Care Diagnostics", J Anal Methods Chem 2019, 2179718, doi:10.1155/2019/2179718 (2019).
Oishee, M. J. et al, "COVID-19 Pandemic: Review of Contemporary and Forthcoming Detection Tools", Infect Drug Resist 14, 1049-1082, doi:10 2147/idr.S289629 (2021).
Phillips, E. A. et al. "Microfluidic rapid and autonomous analytical device (microRAAD) to detect HIV from whole blood samples", Lab Chip 19, 3375-3386, doi:10.1039/c9lc00506d (2019).
Prakash, R., et al, "Integrated sample-to-detection chip for nucleic acid test assays", Biomed Microdevices 18, 44, doi:10.1007/s10544-016-0069-8 (2016).
Primiceri, E. et al., "Key Enabling Technologies for Point-of-Care Diagnostics", Sensors (Basel) 18, doi:10.3390/s18113607 (2018).
Ribeiro, B. V., et al., "Biosensors for the detection of respiratory viruses: A review", Talanta Open. Dec. 2020;2:100007. doi: 10.1016/j.talo.2020.100007. Epub Aug. 16, 2020.
Wang, L. et al, "A sensitive DNA capacitive biosensor using interdigitated electrodes", Biosens Bioelectron 87, 646-653, doi:10.1016/j.bios.2016.09.006 (2016).
Zhang, J. et al, "An interdigitated microelectrode based aptasensor for real-time and ultratrace detection of four organophosphorus pesticides", Biosens Bioelectron 150, 111879, doi:10.1016/j.bios.2019.111879 (2020).
Zhu, H., et al, "Recent advances in lab-on-a-chip technologies for viral diagnosis", Biosens Bioelectron 153, 112041, doi:10.1016/j.bios.2020.112041 (2020).
Zhu, X., et al., "Biosensing approaches for rapid genotoxicity and cytotoxicity assays upon nanomaterial exposure", Small 9, 1821-1830, doi:10.1002/smll.201201593 (2013).
Zupancic, J. M. et al, "Directed evolution of potent neutralizing nanobodies against SARS-CoV-2 using CDR-swapping mutagenesis", Cell Chem Biol 28, 1379-1388.e1377, doi:10.1016/j.chembiol.2021.05.019 (2021).
Feng, K., et al. "Electrochemical immunosensor with aptamer-based enzymatic amplification", Analytical Biochemistry, vol. 378, No. 1, Jul. 1, 2008 (Jul. 1, 2008), pp. 38-42 (2008).

* cited by examiner

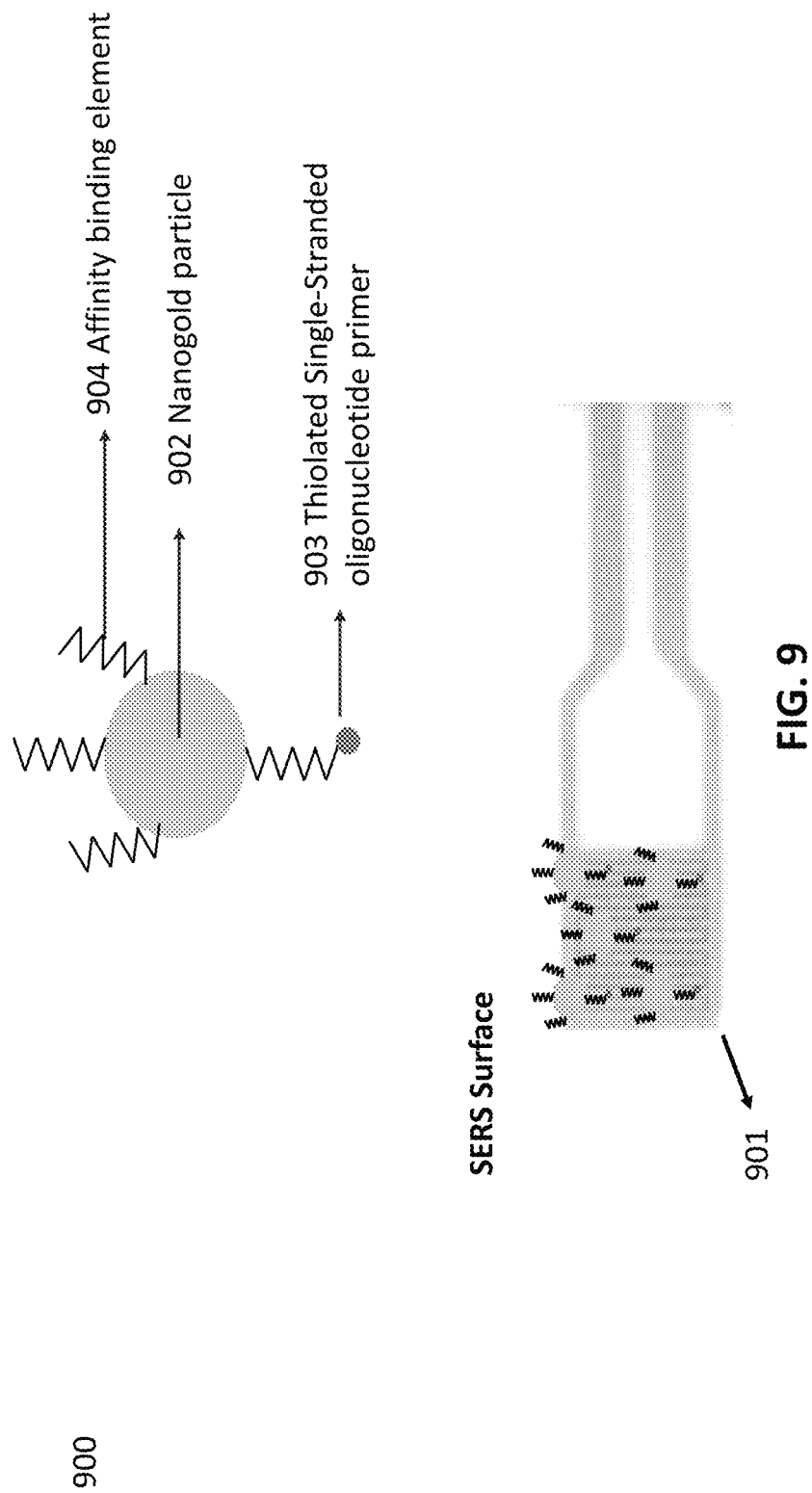

FIG. 13

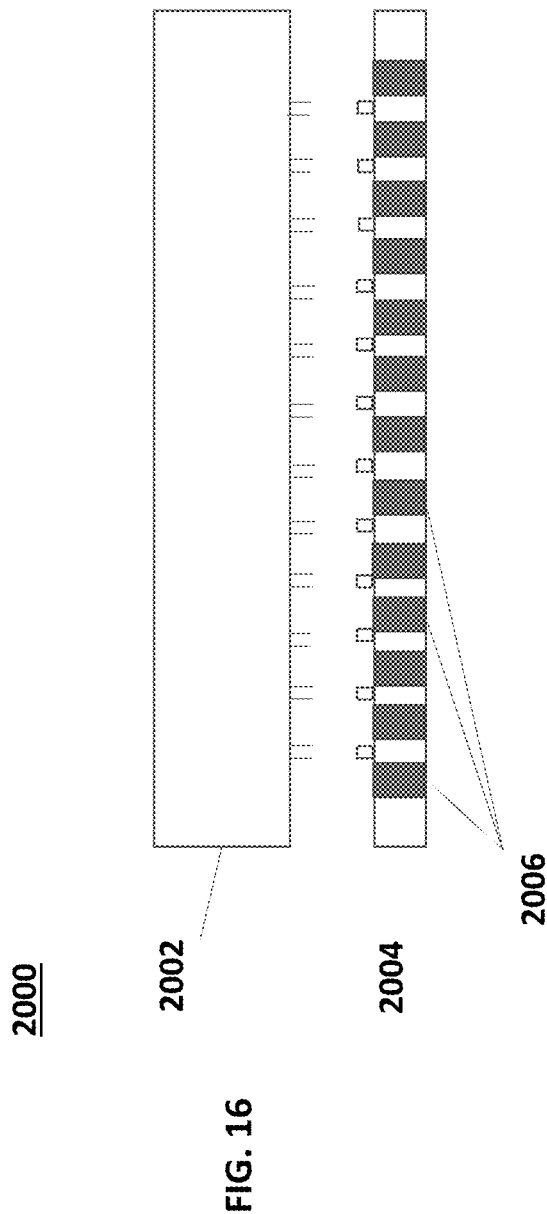

Figure 17

Table 1: SARS-CoV-2 Probe Design

| Name/Target | Target site | ASO sequence | ASO with modifications |
|---|---|---|---|
| CoV2-SPIKE-1712 | ACACTACTGATGCTGTCCGT | ACGGACAGCATCAGTAGTGT | mA*mC*mG*mgmAmCmAmUmCmAmGmUmAmG*mU*mG*mU |
| CoV2-SPIKE-3555 | CCTCAATGAGGTTGCCAAGA | TCTTGGCAACCTCATTGAGG | mU*mC*mU*mUmGmGmCmAmAmCmCmUmCmAmUmUmG*mA*mG*mG |
| CoV2-Nucleocapsid-158 | TCACCGCTCTCACTCAACAT | ATGTTGAGTGAGAGCGGTGA | mA*mU*mG*mUmUmGmAmGmUmGmAmGmAmGmCmGmG*mU*mG*mA |
| CoV2_Nucleocapsid-563 | CACGTAGTCGCAACAGTTCA | TGAACTGTTGCGACTACGTG | mU*mG*mA*mAmCmUmGmUmUmGmCmGmAmCmUmAmC*mG*mU*mG |
| CoV2-Membrane-296 | CTTTCAGACTGTTTGCGCGT | ACGCGCAAACAGTCTGAAAG | mA*mC*mG*mCmGmCmAmAmAmCmAmGmUmCmUmGmA*mA*mA*mG |
| CoV2-Membrane-566 | GTGACTCAGGTTTTGCTGCA | TGCAGCAAAACCTGAGTCAC | mU*mG*mC*mAmGmCmAmAmAmAmCmCmUmGmAmGmU*mC*mA*mC |
| CoV2-Envelope-160 | CCTTCTTTTACGTTTACTCT | AGAGTAAACGTAAAAGAAGG | mA*mG*mA*mGmUmAmAmAmCmGmUmAmAmAmAmGmA*mA*mG*mG |
| CoV2-E ASO-198 | TTCTTCTAGAGTTCCTGATC | GATCAGGAACTCTAGAAGAA | mG*mA*mU*mCmAmGmGmAmAmCmUmCmUmAmGmAmA*mG*mA*mA |
| CoV2-ORF1ab-1256 | AGTGTGCCTATTGGGTTCCA | TGGAACCCAATAGGCACACT | mU*mG*mG*mAmAmCmCmCmAmAmUmAmGmGmCmAmC*mA*mC*mU |
| CoV2_ORF1ab-6736 | TCAACCGCTGCTTTAGGTGT | ACACCTAAAGCAGCGGTTGA | mA*mC*mA*mCmCmUmAmAmAmGmCmAmGmCmGmGmU*mU*mG*mA |
| CoV2_ORF1ab-10098 | TGTTCGCATTCAACCAGGAC | GTCCTGGTTGAATGCGAACA | mG*mU*mC*mCmUmGmGmUmUmGmAmAmUmGmCmGmA*mA*mC*mA |
| NC5 Neg.cont. ASO | | GCGACTATACGCGCAATATG | mG*mC*mG*mAmCmUmAmUmAmCmGmCmGmCmAmAmU*mA*mU*mG | m= 2'-O-Methyl, *Phosphorothioate, A= Adenosine, C= Cytosine, G= Guanidine, T= Thymidine, U= Uracil

Figure 18

| Table 2: Sequences of the selected aptamers (Sequences in bold are primers) | |
|---|---|
| Name | Sequence (5'-3') |
| CoV2-S-RBD-1C | CAGCACCGACCTTGTGCTTTGGGAGTGCTGGTCCAAGGGCGTTAATGGACA (SEQ ID NO: 29) |
| CoV2-S-RBD-4C | ATCCAGAGTGACGCAGCATTTCATCGGGTCCAAAAGGGGCTGCTCGGGATTGCGGATATGGACACGT (SEQ ID NO: 30) |
| COV-N-2 | GCAATGGTACGGTACTTCCGGATGCGGAAACTGGCTAATTGGTGAGGCTGGGGCGTCGTGCAGCAAAAGTGCACGCT (SEQ ID NO: 31) |
| COV-N-3 | GCAATGGTACGGTACTTCCGGATGCGGAAACTGGCTAATTGGTGAGGCTGGGGCGGT (SEQ ID NO: 32) |

Cartridge showing detection/excitation scheme – in reader

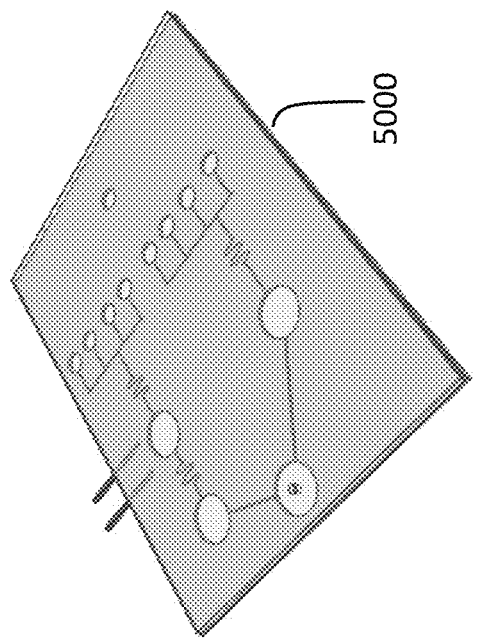
FIG. 21A

Fig 20b insertion into reader

SYSTEMS, APPARATUS, AND METHODS FOR DETECTING PATHOGENS

RELATED APPLICATIONS

The present Application claims the benefit of and priority to U.S. Provisional Patent Application No. 63/082,694, filed on Sep. 24, 2020, and U.S. Provisional Patent Application No. 63/143,690 filed on Jan. 29, 2021. The entire teachings of these earlier applications are incorporated herein by reference.

BACKGROUND

Conventional diagnostic tests for detecting pathogens in samples (e.g., RT-PCR tests applied to biological and environmental samples suffer from various shortcomings. For example, many conventional tests can be time consuming, can require expensive equipment to be used in clinical labs, can require trained personnel to carry out the test, can be costly, and/or can be affected by breakdown of supply-chain and lack of needed specialized reagents. Further, many conventional tests, such as conventional serology tests, can lack a desired sensitivity, which can result in producing a high number of false positives.

SUMMARY

Systems and corresponding methods for detecting one or more target pathogens in a sample are disclosed. The disclosed systems and corresponding methods can identify presence of a target pathogen in a sample by detecting one or more proteins and one or more genetic components (e.g., ribonucleic acid (RNA) and deoxyribonucleic acid (DNA) of the pathogen. The systems and methods disclosed herein overcome the shortcomings in the existing conventional tests by providing comprehensive, robust, accurate, and rapid tests for detecting pathogens.

In some aspects, a disposable cartridge for detecting at least one protein and at least one genetic component associated with a pathogen in a specimen/sample is disclosed. The disposable cartridge includes a cartridge frame that comprises: a sample inlet port for receiving the specimen/sample, a first sensor configured to detect a target protein associated with the pathogen, a second sensor configured to detect a target genetic component associated with the pathogen, a first reservoir for storing a protein buffer for preparing the sample for detection of the target protein, a second reservoir for storing a genetic buffer for preparing the sample for detection of the genetic component, wherein at least one reagent of one of the protein and genetic buffers is absent from the other buffer, and at least one release mechanism coupled to the first and second reservoirs for releasing at least a portion of a liquid in the first reservoir for transfer to the first sensor and for releasing at least a portion of a liquid in the second reservoir for transfer to the second sensor.

A cartridge according to the present teachings can be used in a variety of detection systems, such a point-of-care (POC) diagnostic systems, high-throughput systems for surveillance and/or monitoring and/or diagnostic purposes.

Although in the following discussion a cartridge according to the present teachings is described for analysis of a biological specimen, it should be understood that a cartridge according to the present teachings can be used for analysis of a variety of different types of specimen. For example, the cartridge can be employed for analysis of biological specimens/samples, such liquid biopsy specimens and breath samples, as well as environmental samples, such as air samples and waste water samples.

The cartridge can include a first sample-transfer fluidic channel extending from the sample inlet port to an inlet port of the first reservoir for transferring at least a first portion of the biological specimen to the first reservoir, wherein an interaction of the first portion of the biological specimen with the protein buffer generates a first processed sample.

The cartridge can also include a second sample-transfer fluidic channel configured to deliver at least a second portion of the biological specimen to an inlet port of the second reservoir, wherein an interaction of the second portion of the biological specimen with the genetic buffer generates a second processed sample.

The cartridge can include a first sample-delivery fluidic channel for transferring the first processed sample to the first sensor. The cartridge can include an amplification well in fluid communication with the second reservoir for receiving the second processed sample released from the second reservoir, where the amplification well comprises one or more reagents required for amplification of the one or more genetic components for generating an amplified sample.

The cartridge can include a second sample-delivery fluidic channel for delivering the amplified sample to the second sensor. Further, the cartridge includes any of a heating and a heating and cooling device thermally coupled to the amplification well.

A variety of sensors can be used in a cartridge according to the present teachings. Some examples of such sensors include, without limitation, electrochemical sensors, optical sensors, colorimetric sensors, among others.

Each of the first and the second sensor can be an electrochemical sensor. The first electrochemical sensor can include a working electrode functionalized with a first affinity binding element exhibiting specific binding to the target protein and the second electrochemical sensor can include a working electrode functionalized with a second affinity binding element exhibiting specific bind to the target genetic component.

The first affinity binding element can include any of one or a matched pair of antibodies, one or a matched pair of monobodies, one or a matched pair of nanobodies, an aptamer, a SOMAmer, a raptomer, and a megastar and the second affinity binding element can include an oligonucleotide having a complementary oligonucleotide sequence relative to the target genetic component. Alternatively or additionally, the target genetic component can include any of a DNA and/or an RNA segment.

Further, the biological specimen can be a liquid biopsy. For example, the biological specimen can be a saliva and/or a blood specimen. The biological specimen can also be a breath sample that can be collected and condensed using a breath collection device. A cartridge according to the present teachings can be used for detection of a variety of pathogens, such as viruses and bacteria. By way of example, the virus can be of SARS-CoV-2.

Furthermore, a cartridge according to the present teachings can be configured for communication with an analysis module of the system for transfer of signals generated by the sensors to the analysis module. The analysis module can be configured to operate on the received signals to determine whether a target pathogen is present in a sample under analysis.

In some embodiments, the first sensor can include a first plurality of sensing units for detecting a plurality of different target proteins associated with the pathogen such that each of the sensing units is configured to detect a different one of the plurality of target proteins. The second sensor can include a second plurality of sensing units for detecting a plurality of different target genetic components associated with the pathogen such that each of the second plurality of sensing units is configured to detect a different one of the plurality of genetic components. The first plurality of sensing units can include a plurality of electrochemical sensors each functionalized with a different affinity binding element such that each of the affinity binding elements exhibits specific binding to one of the different target proteins. Further, the second plurality of sensing units can include a plurality of electrochemical sensors each functionalized with a different affinity binding element such that each of the affinity binding elements exhibits specific binding to one of the different target genetic components. Some examples of suitable affinity binding elements can include any of an antibody, an aptamer, a SOMAmer, a nanobody, a monobody, a megastar or combinations thereof. Other examples of affinity binding elements suitable for detection of genetic components of a target pathogen can include, without limitation, oligonucleotides having complementary nucleotide sequences relative to target pathogens of interest.

In some embodiments, a cartridge according to the present teachings may include at least one optically-transparent window to allow optical access to one or more wells and/or sensors incorporated within the cartridge. For example, in some embodiments in which a sensor incorporated in the cartridge is a colorimetric sensor, such transparent window can allow visual inspection of that sensor.

Alternatively or additionally, the cartridge frame can include a polymeric layer in which the above various reservoirs and sensors are incorporated. By way of example, in some embodiments, the polymeric layer may be formed of PDMS or polyurethane, though any other suitable polymer may also be employed.

In a related aspect, a disposable cartridge for use for detecting at least one protein and at least one genetic component associated with a pathogen in a specimen/sample is disclosed, which includes a cartridge frame having a sample-receiving well for receiving the biological specimen, a first reservoir for storing a protein buffer for preparing the specimen/sample for detection of the target protein, a second reservoir for storing a genetic buffer for preparing the sample for detection of the genetic component, wherein at least one reagent of at least one of the protein and genetic buffer is absent from the other buffer. The cartridge can further include a first sample-processing well in fluid communication with the sample-receiving well and the first reservoir for receiving a first portion of the collected sample and at least a portion of the protein buffer, where an interaction of the sample and the protein buffer generates a first processed sample, and a second sample-processing well in fluid communication with the sample-receiving well and the second reservoir for receiving a second portion of the sample and at least a portion of the genetic buffer, where an interaction of the second portion of the sample with the genetic buffer generates a second processed sample. A first sensor is in fluid communication with the first sample-processing well for receiving the first processed sample for detecting the target protein associated with the pathogen, and a second sensor is in fluid communication with the second sample-processing well for receiving the second processed sample for detecting the target genetic component associated with the pathogen.

As discussed above, the cartridge can be used in a variety of detection systems, such point-of-care (POC) diagnostic systems, high-throughput systems for surveillance and/or monitoring and/or diagnostic purposes.

Although in the following discussion a cartridge according to the present teachings is described for analysis of a biological specimen, it should be understood that a cartridge according to the present teachings can be used for analysis of a variety of different types of specimen. For example, the cartridge can be employed for analysis of biological specimens/samples, such liquid biopsy specimens and breath samples, as well as environmental samples, such as air samples and waste water samples.

In some embodiments, the probe can be any of an aptamer, a SOMAmer, an antibody and/or a raptomer, nanobody, monobody, megastars or combinations thereof.

In another aspect, a sensor for detecting a target pathogen (e.g., a virus or a bacterium) in a biological specimen, such as a respiratory sample, is disclosed, which includes at least two sensing units one of which is configured to detect at least one protein (such as a structural protein) associated with the target pathogen and another one is configured to detect at least one RNA and/or DNA segment associated with that pathogen (e.g., an RNA and/or DNA segment that is unique to that pathogen). The sensor can include a chamber having an inlet for receiving specimens. Specimens could be one or more breath samples exhaled by an individual under test. Specimens could be saliva, sputum, nasal secretion (nasal or nasopharyngeal) that is collected in a sample collection tube attached or detached from the cartridge. A reservoir positioned in the chamber can include one or more sample-processing reagents for processing the samples. The reservoir can be formed between a frangible membrane and a valve, which can be actuated to deliver the processed sample to the sensing units. As discussed in more detail below, a sample delivery device can be used to puncture the frangible membrane to deliver the samples to the reservoir.

As discussed in more detail below, in some embodiments, the reservoir can include two chambers that are separated from one another by a partition, where one or more sample-processing reagents for processing the sample for detection of at least one target protein is stored in one chamber (herein such sample-processing reagents are also referred to as a "protein-processing buffer") and one or more sample-processing reagents for processing the sample for the detection of at least one target RNA and/or DNA segment is stored in the other chamber (herein such sample-processing reagents are generally referred to as "RNA/DNA processing buffer or a "genetic processing buffer"). Again, a frangible membrane covering the chambers can be punctured to allow the introduction of the sample(s) (e.g., breath samples) into the two chambers.

Each chamber can include an outlet that is fluidly coupled via one or more fluid channels to a respective sensing unit. More specifically, the chamber in which the protein-processing buffer is stored is coupled via a fluid line to one or more sensing units that are configured in a manner discussed herein to detect at least one protein associated with the target pathogen and the chamber in which the RNA/DNA-processing buffer is stored is coupled via another fluid line to one or more sensing units that are configured in a manner discussed herein to detect one or more RNA and/or DNA sequences of the target pathogen (typically those segments that are unique to that pathogen). An analyzer can receive signals generated by the sensing units to determine whether the target pathogen is present in the sample. More specifically, the analyzer can indicate the presence of the target pathogen in the sample when both the protein-detecting and RNA/DNA detecting sensing units provide positive signals (i.e., signals indicative of the presence of the protein and RNA/DNA segments). The sensing units can be in the form of electrochemical analysis cells according to various embodiments, which are described in detail below.

The above sensor can be coupled to a breath collection device comprising a mouth-nose piece for engaging with a respiratory tract of a user for receiving one or more breath samples from the user and a tube in fluid communication with the mouth-nose piece for receiving the breath sample(s), where the tube being configured for engaging with the sensor for delivering the one or more breath samples to the sensor. Upon insertion, the distal end of the tube into the sensor's chamber, the distal end can puncture the polymeric seal covering the reservoir, thus allowing the collected breath samples to be introduced into the reservoir.

In a related aspect, a sensor is disclosed that includes a housing having a first and second portion and a control valve that is positioned between those portions to control flow of fluid between those portions. The first portion provides a chamber having an opening for receiving a tube of a breath collection device for delivering one or more breath samples exhaled by an individual into the chamber. A reservoir positioned in the chamber can store one or more sample-processing reagents. The reservoir can include a frangible membrane that is configured to be punctured by insertion of the tube into the chamber, thereby allowing the breath sample(s) to be mixed with the reagents stored in the reservoir. At least one electrochemical analysis cell is positioned in the second portion of the housing. An actuator coupled to the control valve can control the valve in order to allow the mixture of the breath sample(s) and the sample-processing reagent(s) to be delivered to the electrochemical analysis cell, where the electrochemical cell is configured to generate a detection signal when at least one target pathogen is present in the breath sample(s).

The electrochemical analysis cell can include a working electrode (herein also referred to as a sensing electrode), a counter electrode and a reference electrode. The working electrode can be functionalized in a manner discussed herein to configured the electrochemical analysis cell for detection of one or more proteins or one or more RNA and/or DNA segments associated with a target pathogen. More specifically, at least one aptamer or at least one oligonucleotide can be coupled to the working electrode, where the at least one aptamer is configured to specifically bind to at least one protein associated with a pathogen and the at least one oligonucleotide comprises a nucleotide sequence that is complementary to a nucleotide sequence of at least one RNA or DNA segment of the pathogen.

In some embodiments, a plurality of carbon nanotubes are disposed on the working electrode, where the plurality of carbon nanotubes are functionalized with at least one aptamer configured to specifically bind to at least one protein associated with a pathogen or functionalized with at least one oligonucleotide having a nucleotide sequence complementary to nucleotide sequence of at least one RNA or DNA segment of the pathogen.

In some embodiments, a sequence-specific oligonucleotide or a protein-specific aptamer will be anchored to SWCNT via oligonucleotide DNA anchors. As an example, 8-15 AT (adenine, thymine) repeats can be used as DNA anchors for the attachment of oligonucleotide, for recognition of specific sequences in the genome of a pathogen, or aptamer, for recognition of specific proteins of a pathogen, to SWCNTs. In some embodiments, nucleic acid spacers or linkers such as spacer 18 also known as HEG spacer (hexaethylene glycol) can be placed at 5' or 3' of the oligonucleotide or the aptamer for coupling to the SWCNT. In addition to single HEG spacer, multiple repeats of HEG spacers, for example, 3 or 5, can be used for configuration of the optimal positioning and optimal presentation of the oligonucleotide or aptamer for the recognition and capture of their target sequence or target protein.

The electrochemical analysis cell generates a detection signal when at least a protein or at least an RNA or DNA segment associated with the pathogen, when present in the sample, binds to at least one of the aptamers or the oligonucleotides, respectively, associated with the working electrode. In some embodiments, the working electrode can be functionalized with a self-assemble monolayer (SAM). By way of example, biotin-SAM can be generated under the surface of a gold or carbon electrode.

In some embodiments, a plurality of different types of aptamers can be coupled to the working electrode, where the aptamers are configured to bind to different epitopes of the target protein. Further, in some embodiments, a plurality of different types of oligonucleotides can be coupled to the working electrode, where the different types of oligonucleotides have complementary sequences to different RNA or DNA segments of the target pathogen.

The systems and methods according to the present teachings can be employed to detect a variety of pathogens, such as viruses and bacteria. For example, such systems and methods can be employed to detect a Coronavirus (e.g., SARA-CoV-2 virus), and an influenza virus in a sample.

In some embodiments, the reservoir is formed between the frangible membrane and the control valve. The frangible membrane can be formed, e.g., of a polymeric material, such as cellophane or polyurethane. The thickness of the frangible membrane can be selected to ensure that proper sealing of the reservoir can be achieved while allowing the membrane to be punctured via application of modest force. For example, the frangible membrane can have a thickness in a range of about 0.5 mm to about 1 mm.

The housing can also be formed of polymeric material. For example, PDMS (polydimethylsiloxane) can be employed for fabricating the housing. comprises a polymeric material.

In some embodiments, the sensor is coupled to a breath collection device that includes a mouth-nose piece for breath collection, which can engage with a respiratory tract of a user for receiving one or more breath samples from the user and a tube in fluid communication with the mouth-nose piece for receiving the one or more breath samples, where the tube is configured for engaging with the sensor for delivering the one or more breath samples to the sensor. A filter can be positioned in the tube for inhibiting at least a portion (and preferably substantially all) of the target pathogen (and other pathogens when present in the breath samples) from exiting into the external environment. In particular, the tube can include a pressure relief valve that can open when the pressure within the mouth-nose piece exceeds a threshold. The filter can be placed upstream of such a pressure relief valve to inhibit the spread of any pathogens present in the breath samples to the external environment.

Further, a one-way valve can be positioned in the tube to prevent a back flow of the one or more reagents stored in the reservoir as the breath sample(s) are introduced into the reservoir.

In the above sensor, the electrochemical cell generates a detection signal when the at least one protein or the at least one RNA or DNA segment associated with the pathogen, when present in the sample, binds to at least one of the aptamers or the oligonucleotide, respectively.

The sensor can further include an analysis module that is in communication with the electrochemical analysis cell to receive the detection signals generated by the electrochemical cell and process those detection signals to determine whether a target pathogen is present in the sample. For example, in some embodiments, when detection signals generated by both the protein-detecting sensing unit and the RNA/DNA-detecting sensing unit exceed certain predefined thresholds, the analyzer can indicate that the target pathogen is present in the sample.

In some embodiments, the sensor can be disposed within a disposable cartridge.

In some embodiments, the sensor can include a plurality of sensing units, where one of the sensing units comprises aptamer-functionalized carbon nanotubes and another one of the sensing units comprises oligonucleotide-functionalized carbon nanotubes. In some such embodiments, the carbon nanotubes are functionalized with a plurality of aptamers that exhibit specific binding to different epitopes of at least one protein of a target pathogen.

In some embodiments, the housing includes a top surface and a bottom surface. In some such embodiments, the working electrode of the electrochemical analysis cell is positioned in proximity of the bottom surface and the reservoir is formed between the breakable membrane and at least a portion of the top surface. The housing can further include a front surface in which an aperture is formed and an opposed back surface. In some such embodiments, the reservoir is formed between the breakable membrane and at least a portion of the opposed back surface.

As noted above, the breakable membrane can be formed of a polymeric material, such as soft polyurethane or other suitable polymers. Further, the housing can be formed of a polymeric material, such as PDMS.

In a related aspect, a method of detecting a pathogen in a respiratory sample is disclosed, which comprises collecting one or more breath samples from an individual, mixing the breath sample(s) with one or more reagents to prepare at least one pathogen, when present in the breath sample(s), for detection, introducing at least a portion of the mixture into an electrochemical cell that is configured to detect at least one protein associated with the pathogen and introducing another portion of the mixture into an electrochemical cell that is configured to detect at least one RNA and/or DNA segment associated with the pathogen, where each of the electrochemical cells generates a detection signal in response to the detection of the protein(s) and/or the RNA/DNA segment(s). When both electrochemical cells generate positive detection signals indicative of the presence of the pathogen in a sample under study, the presence of the pathogen in the sample is confirmed.

In a related aspect, a method for identifying emergent variants of Coronavirus is disclosed, which comprises introducing a portion of a biological specimen onto a plurality of single-walled carbon nanotubes functionalized with at least one aptamer exhibiting specific binding to at least one structural protein of a known variant of Coronavirus, wherein the structural protein exhibits a homology of at least about 80%, or at least about 90%, among different known variants of Coronavirus, monitoring at least one physical or chemical property of the aptamer-functionalized plurality of carbon nanotubes in response to interaction with the biological specimen to determine whether the structural protein is present in the sample, introducing another portion of the biological specimen onto a plurality of single-walled carbon nanotubes functionalized with a plurality of different oligonucleotide sequences, where each of the oligonucleotide sequences is complementary to an RNA segment that is unique to one of known Corona viruses. This can be followed by monitoring at least one physical or chemical property of the oligonucleotide-functionalized carbon nanotubes to determine whether any of the RNA segments is present in the sample, where an absence of the RNA segments and presence of the at least one structural protein indicates presence of an emergent variant of Coronavirus in that sample. A similar approach can be employed for the detection of emergent variants of other pathogens, where one or more proteins exhibiting a high homology among different variants of that pathogen are available.

In a related aspect, a system for detecting pathogen(s) in a biological specimen other than breath samples is disclosed in which a sensor according to the present teachings can receive such biological specimens. An example of such a sample collection device configured for the collection of saliva samples is discussed in more detail below. A sensor according to the present teachings can also be employed to detect pathogen(s) in blood and urine, among other biological specimens. For example, in some embodiments, conventional sample collection devices can be employed to collect blood and/or urine samples, and the collection samples can be introduced in one or two reservoirs of a sensor according to the present teachings, e.g., using a syringe or other suitable implements.

In another aspect, an air monitoring system is disclosed, which comprises an air collection module providing a chamber for receiving one or more samples of ambient air, at least one sensor configured for removable coupling to the air collection module, the sensor comprising an inlet actuable valve separating the sensor from the chamber upon coupling of the sensor to the air collection module such that the actuation of the inlet actuable valve allows introduction of at least a portion of the air contained in the chamber into the sensor. The sensor can include at least a first sensing unit that is configured for detecting at least one protein associated with a target biological particle, when the biological particle is present in the sampled air, and at least a second sensing unit configured for detecting at least one genetic component of the target biological particle, when the target biological particle is present in the sampled air.

The air collection module can further include at least one air intake port through which ambient air can enter the chamber. In some embodiments, a filter can be positioned relative to air intake port such that the ambient air passes through the filter before entering the chamber. Further, in some embodiments, the system can include an impeller positioned in proximity of the air intake port for facilitating the introduction of the ambient air through the port into the chamber.

In some embodiments, the biological particle can be a pathogen, e.g., a bacterium or a viral particle.

Further, the first sensing unit can include at least one sensing module in the form of an electrochemical sensor having a sensing electrode that is functionalized with at least one affinity binding element that exhibits specific binding to at least one protein associated with the biological particle. The sensing electrode can be functionalized with a variety of different affinity binding elements. For example, the affinity binding elements can be an aptamer, an oligonucleotide, a morpholino, and/or an affirmer, though any suitable affinity binding element that can exhibit specific binding to a protein of interest can be employed. In some embodiments, such an affinity binding element can exhibit a binding affinity in low nanomolar range (10-9) to picomolar range (10-12).

The first sensing unit can include a plurality of sensing modules where the sensing modules are functionalized with different affinity binding elements such that each of the sensing modules is capable of detecting a different protein associated with the biological particle of interest. In this manner, a multiplexed sensing unit can be fabricated, which allows concurrent detection of multiple proteins associated with the biological particle.

The second sensing unit can include at least one sensing module having an electrochemical sensor having a sensing electrode functionalized with at least one affinity binding element exhibiting specific binding to at least one genetic component of the biological particles, e.g., an RNA and/or a DNA segment. By way of example, such an affinity binding element can be an oligonucleotide having a nucleotide sequence that is complementary to the nucleotide sequence of the target genetic component.

The sensor can include a porous impaction material and a nozzle positioned downstream of the inlet valve through which a received air sample can be accelerated toward the porous impaction material, wherein the porous impaction material is configured to separate the at least one target biological particle, when present in the received air sample, from at least some of the other particulates present in the air sample such that at least a portion of the target biological particle can reach a capture filter that is positioned downstream of the impaction material.

The impaction material and the capture filter can be placed in an enclosure (herein also referred to as a well). In some such embodiments, a buffer reservoir for storing a buffer suitable for removing at least a portion of the captured biological particle from the capture filter is positioned relative to the enclosure (well) such that the stored buffer can be released into the enclosure upon actuation of a valve separating the buffer from the enclosure such that the buffer can come into contact with the capture filter and release at least a portion of the target biological particle from the filter into the buffer (the mixture of the buffer and the released biological particles is herein referred to as a "buffer sample").

The enclosure can include a surface in which a valve is disposed so as to regulate the introduction of the buffer sample into a downstream conduit, which in turn leads via two branches thereof to two reservoirs in which processing reagents are stored. The processing reagent(s) in one of the reservoirs is suitable for the extraction of at least one genetic component (e.g., an RNA or DNA segment) associated with the biological particle and the processing reagent(s) in the other reservoir is suitable for facilitating the detection of at least one protein associated with the biological particle.

Each of the two reservoirs includes an inlet valve and an outlet valve, where upon actuation of the inlet valve, a portion of the buffer sample flows into the respective reservoir to mix with the processing reagent(s) stored in that reservoir to generate a protein test sample or a genetic test sample. Upon actuation of the outlet valve of each reservoir, the respective test sample can be introduced into a respective sensing unit. More particularly, the protein test sample can be introduced into the sensing unit that is configured to detect one or more proteins and the genetic test sample can be introduced into the sensing unit that is configured to detect at least one genetic component of the biological particle.

The system can further include at least one detector that is in communication with the sensing modules of the sensing units for measuring at least one electrical property of any of the electrochemical sensors of the sensing units and generate one or more detection signals that are indicative of the measured electrical property. In some embodiments, the electrical property can be, for example, the impedance of the electrochemical sensor associated with a sensing module, where the impedance can change in response to interaction of a target biological particle with the working electrode of the sensor.

Each sensing unit can have its dedicated detector for measuring one or more electrical properties of the sensing modules of the sensing unit and generating detection signals in response to such measurements. Alternatively, the sensor can include a single detector that can interrogate the electrochemical sensors of the sensing units, e.g., serially, via a multiplexer that couples that detector to those sensing modules.

The air monitoring system can further include a controller that is in communication with the multiplexer to control the multiplexer such that the multiplexer can couple the detector to the sensing modules in a serial manner such that the detector can interrogate the sensing modules one at a time. The controller is also in communication with the detector to receive the detection signals generated by the detector. The controller is further configured to process the detection signal(s) to determine whether the detection signal is indicative of the detection of a protein or a genetic component associated with a target biological particle by the sensing module generating the detection signal(s).

Alternatively or additionally, the air monitoring system can further include an alarm system that is in communication with the controller so as to generate an alarm signal in response to a control signal generated by the controller that is indicative of the detection of a target biological target in the sampled ambient air. In some embodiments, the alarm system and the controller are implemented as an integrated unit. In other embodiments, the alarm system and the controller can be remote from one another and in communication with one another via one or more communications modules of the air monitoring system. A variety of communication protocols, including a number of known wireless communication protocols, can be employed for establishing a communication link between the controller and the alarm system.

In another aspect, a sensor for detecting an analyte is disclosed, which includes at least one sensing unit comprising a sensing electrode that is functionalized with at least a first affinity binding element exhibiting specific binding to the analyte such that a binding of the analyte to the affinity binding element changes at least one electrical property of the sensing electrode, and at least another sensing unit that comprises a surface for performing surface enhanced Raman spectroscopy (SERS), where the SERS surface is functionalized with at least a second affinity binding element exhibiting specific binding to the analyte for obtaining a Raman signal associated with any of the analyte and the affinity binding element in response to binding of the analyte to the functionalized SERS surface. In some such embodiments, the electrochemical and the Raman sensing is achieved using a single electrode that is a working electrode of an electrochemical sensor and is also configured as a SERS substrate.

In some embodiments, the first and the second affinity binding elements are the same, while in other embodiments, the first affinity binding element can be different from the second affinity binding element.

The sensor can further include a laser (e.g., a diode laser) that can generate radiation that is suitable for exciting at least one Raman active mode of any of the analyte and the affinity binding element. The sensor can further include a photodetector for detecting Raman scattered radiation generated in response to the excitation of the at least one Raman active mode and generating at least one Raman detection signal.

The sensor can also include another detector (herein referred to for ease of description as an "electrical detector") that is in communication with the sensing electrode for measuring the electrical property of the sensing electrode and generating a detection signal indicative of the measured property (e.g., a change in the electrical resistance of the sensing electrode).

The sensor can also include an analyzer in communication with the photodetector and the electrical detector for receiving the Raman as well as the electrical detection signal and processing those signals to determine whether any of the Raman detection signal and the electrical detection signal is indicative of the specific binding of an analyte (e.g., a target pathogen) to the affinity binding element. In some embodiments, the analyzer is configured to indicate the presence of the analyte in a sample under investigation when both the Raman and the electrical signals indicate the presence of the analyte in the sample.

In some aspects, a sensor is disclosed. The sensor includes a housing comprising a first portion and a second portion, a control valve positioned between the first and second portions, the first portion providing a chamber having an opening for receiving a tube of a breath collection device for delivering one or more breath samples of an individual into the chamber, a reservoir positioned in the chamber for storing one or more sample-processing reagents, the reservoir having a frangible membrane configured to be punctured by insertion of the tube into the chamber thereby allowing the one or more breath samples to be mixed with the one or more sample-processing reagents, an electrochemical cell positioned in the second portion, and an actuator coupled to the control valve for controlling the valve in order to allow the mixture of the one or more breath samples and the one or more sample-processing reagents to be delivered to the electrochemical cell, wherein the electrochemical cell is configured to generate a detection signal when at least one target pathogen is present in the one or more breath samples.

In another aspect, a system for detecting a pathogen in a respiratory sample is disclosed. The system includes a sensor configured to detect a target pathogen in a sample and a breath collection device comprising a mouth-nose piece for engaging with a respiratory tract of a user for receiving one or more breath samples from the user and a tube in fluid communication with the mouthpiece for receiving the one or more breath sample, the tube being configured for engaging with the sensor for delivering the one or more breath samples to the sensor. The sensor includes a housing comprising a first portion and a second portion, a control valve positioned between the first and second portions, the first portion providing a chamber having an opening for receiving a tube of a breath collection device for delivering one or more breath samples of an individual into the chamber, a reservoir positioned in the chamber for storing one or more sample-processing reagents, the reservoir having a frangible membrane configured to be punctured by insertion of the tube into the chamber thereby allowing the one or more breath samples to be mixed with the one or more sample-processing reagents, an electrochemical cell positioned in the second portion, an actuator coupled to the control valve for controlling the valve in order to allow the mixture of the one or more breath samples, and the one or more sample-processing reagents to be delivered to the electrochemical cell, wherein the electrochemical cell is configured to generate a detection signal when at least one target pathogen is present in the one or more breath samples.

In yet another aspect, a sensor is disclosed. The sensor includes a housing, and at least one sensing unit disposed within the housing. The sensing unit includes at least one electrochemical cell having a working electrode, a counter electrode and a reference electrode, at least one aptamer or at least one oligonucleotide coupled to the working electrode, wherein the at least one aptamer is configured to specifically bind to at least one protein associated with a pathogen and the at least one oligonucleotide comprises a nucleotide sequence that is complementary to a nucleotide sequence of at least one RNA or DNA segment of the pathogen, an aperture disposed in the housing for receiving an implement configured for collecting a biological sample, at least one internal ledge positioned in the housing for separating the implement from the electrodes once the implement is received in the housing, and a reservoir for storing reagents for processing the biological sample, the reservoir having a breakable membrane, wherein the reservoir is positioned within the housing and the implement is configured such that the implement punctures the membrane once inserted into the housing for releasing at least a portion of the reagents onto at least a portion of the implement so as to introduce at least a portion of the biological sample onto the functionalized working electrode.

In some aspects, a system for detecting a pathogen is disclosed. The system includes a breath input device for engaging in direct communication with a respiratory tract of a user for receiving one or more breath samples from the user, the breath input device comprising a channel for receiving an implement for collecting at least a portion of aerosols, if any, present in the one or more breath samples, and a sensor. The sensor includes a housing and at least one sensing unit disposed within the housing. The sensing unit includes at least one electrochemical cell having a working electrode, a counter electrode and a reference electrode, at least one aptamer or at least one oligonucleotide coupled to the working electrode, wherein the at least one aptamer is configured to specifically bind to at least one protein associated with a pathogen and the at least one oligonucleotide comprises a nucleotide sequence that is complementary to a nucleotide sequence of at least one RNA or DNA segment of the pathogen, an aperture disposed in the housing for receiving the implement, at least one internal ledge positioned in the housing for separating the implement from the electrodes once the implement is received in the housing, and a reservoir for storing reagents for a biological sample, when present in the collected aerosols, the reservoir having a breakable membrane, wherein the reservoir is positioned within the housing and the implement is configured such that the implement punctures the membrane once inserted into the housing for releasing at least a portion of the reagents onto at least a portion of the implement so as to introduce at least a portion of the biological sample onto the functionalized working electrode.

In some aspects, a sensor is disclosed. The sensor includes a housing, and at least one sensing unit disposed within the housing. The sensing unit includes at least one electrochemical cell having a working electrode, a counter electrode, a reference electrode, a plurality of carbon nanotubes disposed on at least one of the working electrode, the plurality of carbon nanotubes being functionalized with at least one aptamer configured to specifically bind to at least one protein associated with a pathogen or functionalized with at least one oligonucleotide having a nucleotide sequence complementary to nucleotide sequence of at least one RNA or DNA segment of the pathogen, an aperture disposed in the housing for receiving an implement configured for collecting a biological sample, at least one internal ledge positioned in the housing for separating the implement from the electrodes once the implement is received in the housing, and a reservoir for storing one or more reagents for processing the biological sample, the reservoir having a breakable membrane, wherein the reservoir is positioned within the housing and the implement is configured such that the implement punctures the membrane once inserted into the housing for releasing at least a portion of the reagents onto at least a portion of the implement so as to introduce at least a portion of the biological sample onto the functionalized working electrode.

In some aspects, a method of detecting a pathogen in a respiratory sample is disclosed. The method includes collecting one or more breath samples from an individual, mixing the one or more breath samples with one or more reagents to prepare at least one pathogen, when present in the one or more breath samples, for detection, and introducing at least a portion of the mixture into an electrochemical cell that is configured to detect at least one protein and at least one RNA segment associated with the pathogen, when present in the one or more breath samples, wherein the electrochemical cell generates a first detection signal in response to the detection of the at least one protein and a second detection signal in response to the detection of the at least one RNA segment.

In some aspects, a method for identifying emergent variants of Corona viruses is disclosed. The method includes introducing a portion of a biological sample onto a plurality of single-walled carbon nanotubes functionalized with at least one aptamer exhibiting specific binding to a structural protein of a known variant of Corona virus, wherein the structural protein exhibits a homology of at least about 80% among different known variants of Corona virus, monitoring at least one physical or chemical property of the aptamer-functionalized plurality of carbon nanotubes in response to interaction with the biological sample to determine whether the structural protein is present in the sample, introducing a portion of the biological sample onto a plurality of single-walled carbon nanotubes functionalized with a plurality of different oligonucleotide sequences, where each of the oligonucleotide sequences is complementary to an RNA segment that is unique to one of known Corona viruses, and monitoring at least one physical or chemical property of the oligonucleotide-functionalized carbon nanotubes to determine whether any of the RNA segments is present in the sample, wherein an absence of the RNA segments and presence of the at least one structural protein indicates presence of an emergent variant of Corona virus in the sample.

In some aspects, an air monitoring system is disclosed. The air monitoring system includes an air collection module providing a chamber for receiving one or more samples of ambient air, at least one sensor configured for removable coupling to the air collection module, wherein the sensor comprises an inlet actuable valve separating the sensor from the chamber upon coupling of the sensor to the air collection module such that actuation of the inlet actuable valve allows introduction of at least a portion of the air contained in the enclosure into the sensor. The sensor includes at least a first sensing unit configured for detecting at least one protein associated with a target biological particle, when the biological particle is present in the sampled air, and at least a second sensing unit configured for detecting at least one genetic component of the target biological particle, when the target pathogen is present in the sampled air.

In some aspects, a sensor for detecting an analyte is disclosed. The sensor includes at least one sensing unit comprising a sensing electrode functionalized with at least a first affinity binding element exhibiting specific binding to the analyte such that a binding of the analyte to the affinity binding element changes at least one electrical property of the sensing electrode, and at least one sensing unit comprising a surface enhanced Raman surface (SERS) functionalized with at least a second affinity binding element exhibiting specific binding to the analyte for obtaining a Raman signal associated with any of the analyte and the affinity binding element in response to binding of the analyte to the functionalized SERS.

Further understanding of various aspects of the present teachings can be obtained by reference to the followed detailed description in conjunction with the associated drawings, which are described briefly below.

BRIEF DESCRIPTION OF THE DRAWINGS

FIG. 9 schematically depicts a sensing electrode that functions both as an electrical sensing electrode as well as a Raman sensing electrode.

Figure 13:
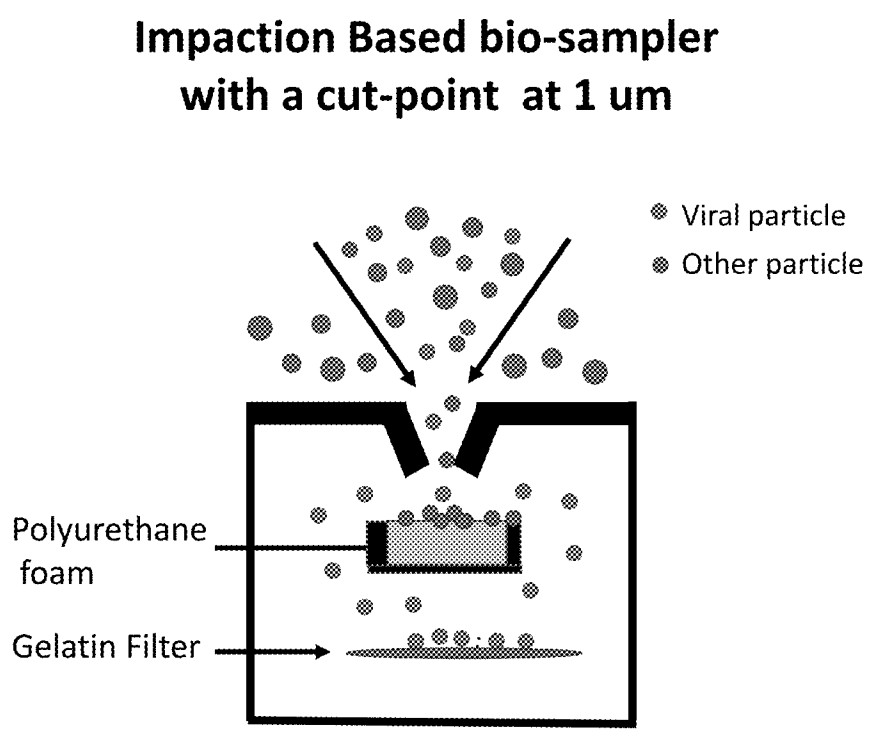

FIG. 13 schematically depicts a portion of the sensing unit shown in FIG. 12, illustrating an impaction material and a capture filter positioned downstream of the impaction material.

FIG. 16 schematically depicts an embodiment of an air monitoring system according to the present teachings, in which a cartridge containing a plurality of sensing units can be removably coupled to a housing of the air monitoring system.

FIG. 17 presents a table containing nucleotide sequences of a plurality of primers suitable for detection of various proteins of a coronavirus.

FIG. 18 presents a table containing nucleotide sequences of a plurality of aptamers suitable for use in the practice of some embodiments of the present teachings.

FIG. 21A schematically depicts a diagnostic system according to an embodiment, which includes a disposable cartridge and a console that receives the cartridge subsequent to introduction of a biological sample onto the cartridge.

DETAILED DESCRIPTION

Figure 1A:
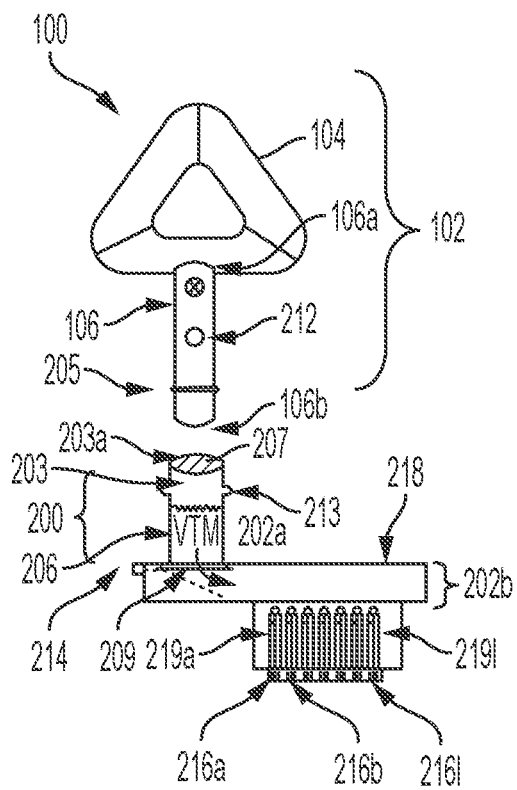
FIGS. 1A, 1B, 1C and 1D, schematically depict a system according to embodiments disclosed herein.
Figure 1B:
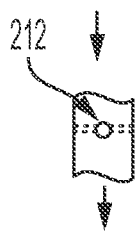
Figure 1C:
Figure 1D:
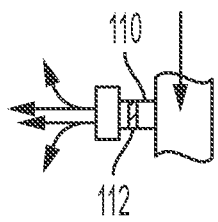

The present disclosure is generally directed to systems and methods for detection of a variety of biomarkers, including disease biomarkers, such as pathogens. In the following discussion, some embodiments of the present teachings are described in connection with the detection of SARS-CoV-2 virus. It should be understood that the present teachings are not limited to the detection of a particular biomarker, but rather provide a platform that can be utilized to detect a variety of biomarkers, including proteins, nucleic acids, small molecules and volatile organic gases, that are components of pathogens such as viruses, bacteria, among others.

As discussed in more detail below, some embodiments provide devices that can allow multiplexed detection of one or more proteins and one or more genetic components of a pathogen, when present in a sample, within a single instrument. In some implementations, such a device can include at least two reservoirs in one of which one or more processing reagents suitable for processing a sample for detection of one or more target protein(s) is stored and in another, one or more processing reagents suitable for processing a sample for detection of one or more target genetic component(s) are stored. Such a device can further include a mechanism for selectively releasing the processing reagent(s) from each reservoir to be mixed with a sample under study to prepare the sample for analysis by a detector (e.g., an electrochemical detector or colorimetric detector) incorporated in the device.

The biosensor and detector units of a system according to the present teachings can be multiplexed so that multiple components of a pathogen or multiple components of multiple pathogens can be detected in one device and the presence or absence of the pathogen (s) be determined. A local reporting or alarming system or wireless reporting will be provided for secure reporting of the presence of pathogen(s).

By way of example, in some embodiments, a cartridge according to the present teachings can include a plurality of sensors (sensing units) each of which is functionalized to detect a different proteins and/or a genetic component of a target pathogen and/or those of a plurality of different target pathogens. In other words, in some embodiment, a cartridge according to the present teachings allows multiplexed detection of various biomarkers associated with a target pathogen and/or multiplexed detection of biomarkers associated with different pathogens.

As discussed in more detail below, in some embodiments, a system according to the present teachings can include a breath collection device for collecting one or more breath samples of an individual and a sensor that includes at least one sensing unit for detecting a protein associated with a target pathogen and at least one sensing unit for detecting an RNA and/or DNA segment associated with that target pathogen. The detection of both a protein and an RNA and/or DNA segment can allow for a more robust detection and identification of a target pathogen and reduce false results. More specifically, in some embodiments, the system can include at least one sensing unit having one or more electrochemical analysis cells that are functionalized to detect one or more proteins of a target pathogen that could be the sign of an active infection and at least another sensing unit having one or more electrochemical analysis cells that are functionalized to detect one or more RNA and/or DNA segments of a target pathogen.

Although in many embodiments discussed below a sensor according to the present teachings is used to detect pathogen(s) in breath samples, such a sensor can also be employed to detect pathogen(s) in other biological specimens/liquid biopsy (e.g., saliva, urine and blood). For example, FIG. 7 discussed in more detail below depicts a saliva collection device, which can be coupled to a sensor according to the present teachings for determining whether a target pathogen is present in a saliva sample. In other embodiments, the present teachings can be utilized to detect a target biomarker in a blood sample.

Various terms are used herein in accordance with their ordinary meanings in the art. For example, the term "aptamer" refers a nucleotide polymer with a specific affinity for a particular target molecule.

The term "nanoparticle," as used herein, refers to a material structure having a maximum dimensional size (e.g., a diameter or other cross-dimensional size) that is equal to or less than about 1 micron, e.g., in a range of about 100 nanometers to about 500 nanometers, or in a range of about 200 nanometers to about 600 nanometers, or in a range of about 300 nanometers to about 700 nanometers, or in a range of about 400 nanometers to about 800 nanometers.

The term "affinity binding element," as used herein, refers to a material structure, e.g., a polymer, that can exhibit a specific binding to an analyte. As discussed in more detail below, some examples of affinity binding elements include, without limitation, aptamers and other oligonucleotides, antibodies. In some embodiments, the affinity binding element can be a monobody that is generated using phage display technology to exhibit a high specific binding to an analyte and/or an organism. In some embodiments that affinity binding element can be a nanobody that is generated in Llama. In some embodiments that affinity binding element can be a megastar for delivering pairs of affinity reagents that can sandwich the target.

The term "substantially," as used herein, refers to state or condition that differs, if any, from a complete state or condition by at most 10%.

The term "buffer" is used herein to refer generally to a processing liquid that includes one or more reagents for preparing a sample for analysis. For example, the term a "protein buffer" is used herein to refer to a buffer that is suitable for processing (preparing) a specimen/sample for detection of one or more proteins therein and the term a "genetic buffer" is used herein to refer to a buffer that is suitable for processing (preparing) a specimen/sample for detection of one or more genetic components (e.g., RNA and/or DNA segments) therein.

With reference to FIGS. 1A, 1B, 1C, and 1D, a system 100 according to an embodiment for detecting a pathogen in a respiratory sample includes a breath collection device 102 comprising a mouth-nose piece 104 (e.g., a mask) for engaging with a respiratory tract of a user for receiving one or more breath samples from the user and a tube 106 that is in fluid communication with the mouth-nose piece for receiving the breath sample(s). The tube 106 extends from a proximal opening 106a for receiving the breath sample(s) exhaled by a user to a distal opening 106b that is configured to engage with a sensor 200.

In this embodiment, the sensor 200 includes a housing 202 formed of a first portion 202a and a second portion 202b. The first portion 202a includes a chamber 203, which in this embodiment is in the form of a substantially cylindrical conduit, having an opening 203a that is configured to releasably engage with the distal opening 106b of the tube 106. An O-ring 205 coupled to the tube 106 in proximity of its distal end can engage with a groove 213 formed in proximity of the proximal end of the chamber 203 to provide a sealing engagement between the tube 106 and the chamber 203.

With continued reference to FIG. 1A, a reservoir 206 positioned within the chamber 203 can store one or more sample-processing reagents. In this embodiment, the reservoir 206 is formed between a frangible membrane 207 and a flapper valve 209.

Referring again to the breath collection device 102, a breath-through valve 110 (herein also referred to as a "pressure-relief valve") allows egress of the gas exhaled into the mouth-nose piece 104 into the external environment when the pressure within the mouth-nose piece exceeds a threshold. A filter 112 positioned upstream of the pressure-relief valve inhibits, and preferably prevents, the passage of pathogens, if any, present in the exhalation gas into the external environment. In some cases, such pathogens can be present in the exhaled air as aerosols (i.e., as suspension of tiny particles or droplets).

By way of example, in this embodiment, a 0.2-micron filter marketed by Pall Corporation of Westborough, Mass. under the trade designation Supor® membrane can be employed to inhibit the transfer of pathogens (e.g., viral particles), if any, to the external environment.

Referring now to the sensor 200, the frangible membrane 207 that covers the proximal opening 203a of the chamber 203 to seal the internal components of the sensor from the external environment in absence of engagement of the breath collection device with the sensor can be formed of a variety of different polymeric materials, such as soft polyurethane.

The distal end of the tube 106 can be used to puncture the polymeric seal 207 for inserting the distal end of the tube 106 into the proximal end of the chamber 203 so as to engage the tube 106 with the chamber 203 while the O-ring 205 provides a seal. Upon engaging with the chamber 203, the distal end of the tube 106 also punctures the frangible membrane 207, thus allowing the breath samples to be mixed with the reagent(s) stored in the reservoir 206. A one-way valve 212 provided in the tube 106 of the breath collection device can inhibit the backflow of the mixture of the breath samples and the reagents. As discussed in more detail below, by way of example, the reservoir 206 can contain a virus transfer medium (VTM) to which one or more reagents for processing the sample are added.

An actuator 214, such as a mechanical actuator (e.g., a release button), can be used to open the flapper valve 209, thus releasing at least a portion of the mixture of the breath samples and the sample-processing reagents into the second portion 202b of the sensor's housing. A plurality of electrochemical analysis cells 216a, 216b, . . . , 216l (herein referred to collectively as electrochemical analysis cells 216) are positioned in the second portion of the sensor's housing so as to receive at least a portion of the mixture released into the second portion of the housing via activation of the flapper valve 209.

More specifically, the second portion 202b of the housing includes a central conduit 218 that receives the sample released via opening the flapper valve 209. A plurality of peripheral conduits 219a, 219b, . . . , 219i (herein referred to collectively as peripheral conduits 219), each of which extends from the central conduit 218 to one of the electrochemical analysis cells 216, delivers a portion of the sample to each of the electrochemical cells.

As discussed in more detail below, each of the electrochemical cells 216 is configured to detect at least one protein associated with a target pathogen or at least one RNA and/or DNA segment associated with that pathogen, when the pathogen is present in the collected breath samples. By way of example, at least one of the electrochemical cells 216 can be configured for detecting at least one protein and at least one of the electrochemical cells 216 can be configured for detecting at least one RNA and/or one DNA associated with the pathogen.

Figure 2A:
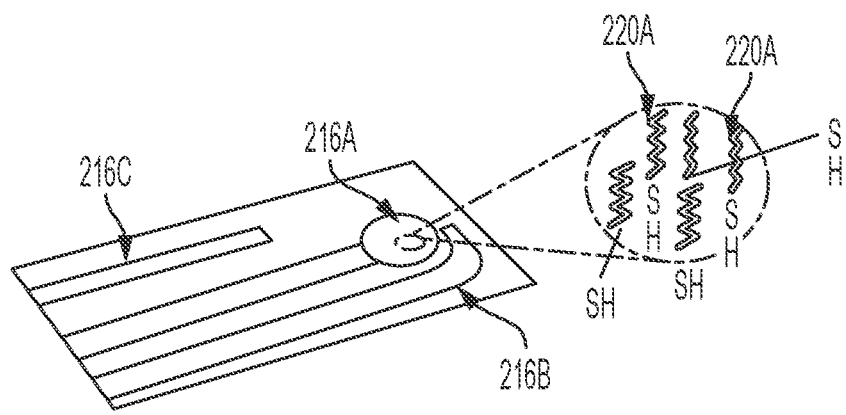
FIG. 2A schematically depicts an electrochemical analysis cell according to an embodiment in which the working electrode of the cell is functionalized with a plurality of oligonucleotide probes.
Figure 2B:
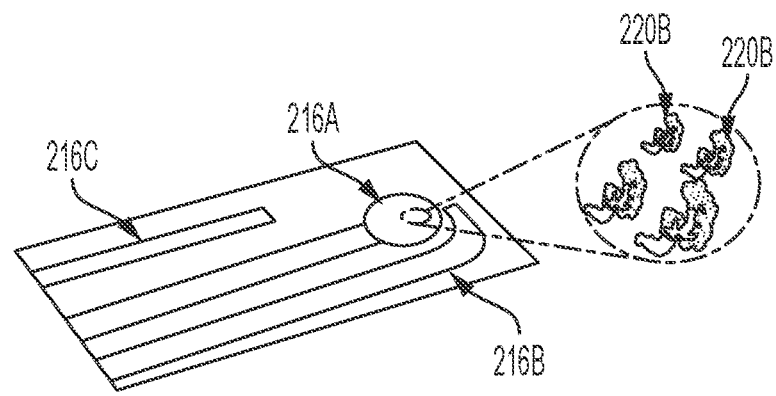
FIG. 2B schematically depicts an electrochemical analysis cell according to an embodiment in which the working electrode of the electrochemical analysis cell is functionalized with a plurality of aptamer probes.
Figure 3A:
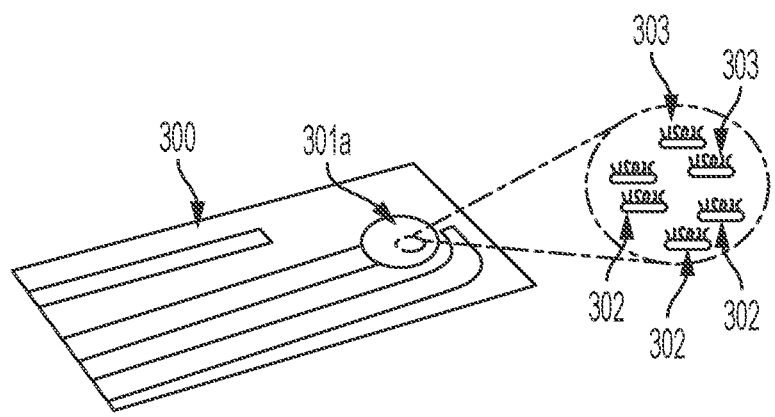
FIG. 3A schematically depicts an electrochemical analysis cell according to an embodiment in which the working electrode of the electrochemical analysis cell is functionalized with a plurality of carbon nanotubes, which are in turn functionalized with a plurality of aptamers.
Figure 3B:
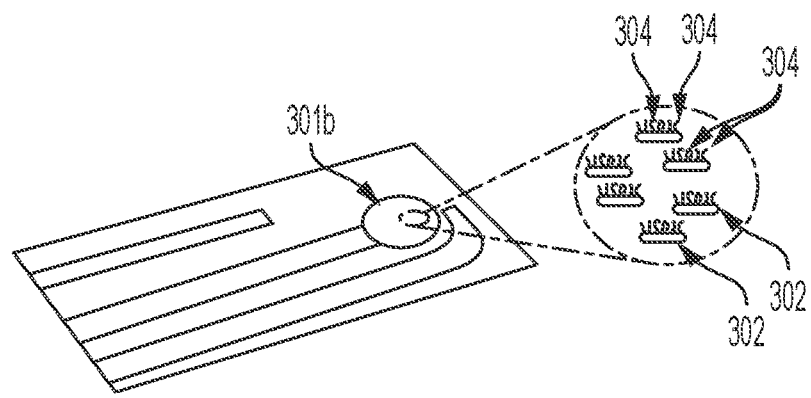
FIG. 3B schematically depicts an electrochemical analysis cell according to an embodiment in which the working electrode of the cell is functionalized with a plurality of carbon nanotubes, which are in turn functionalized with a plurality of oligonucleotide probes.
Figure 4A:
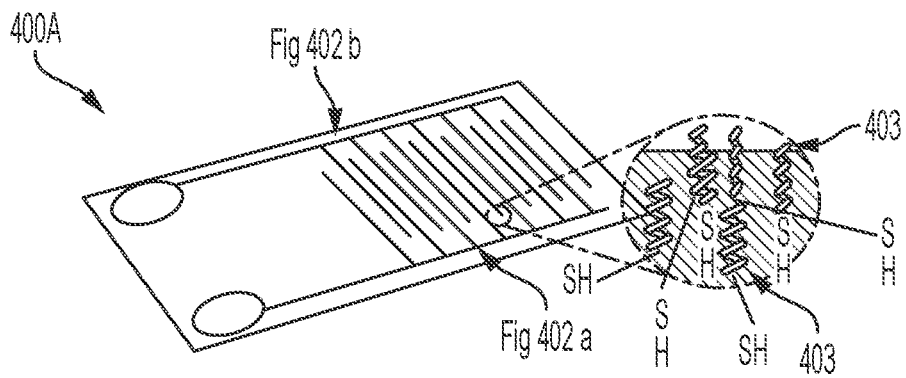
FIG. 4A schematically depicts an electrochemical cell comprising two interdigitated electrodes, where one of the electrodes is functionalized with a plurality of aptamer probes.
Figure 4B:
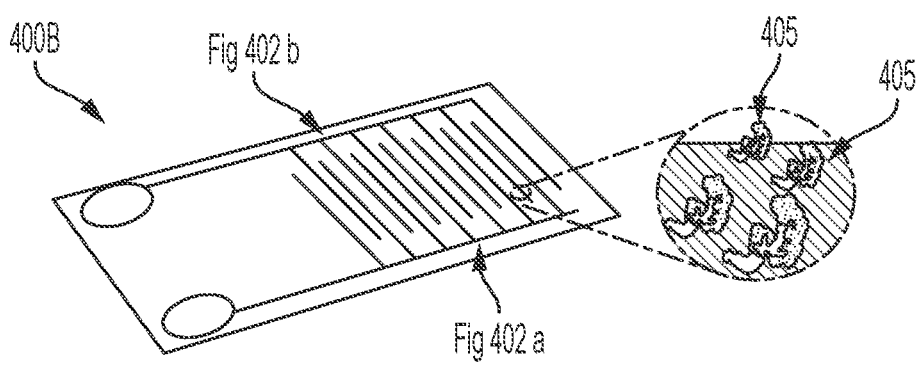
FIG. 4B schematically depicts an electrochemical cell comprising two interdigitated electrodes, where one of the electrodes is functionalized with a plurality of oligonucleotide probes.
Figure 5:
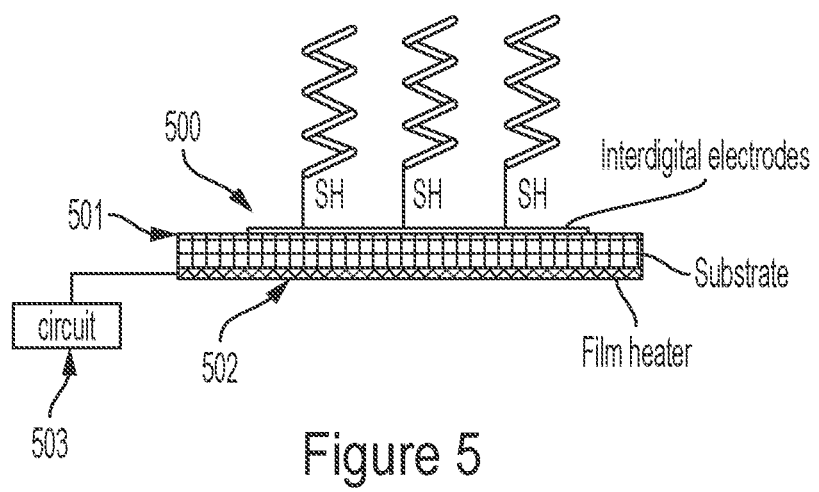
FIG. 5 is a partial schematic view of an electrochemical cell in which a heating element is disposed underneath the cell's working electrode for heating thereof.

More specifically, with reference to FIGS. 2A, and 2B, in some embodiments, any of the electrochemical analysis cell 216 (herein also referred to as a potentiostat) includes a working electrode 216a (herein also referred to as a sensing electrode), a counter electrode 216b, and a reference electrode 216c. A plurality of biorecognition elements (herein also referred to as affinity binding elements, e.g., oligonucleotides 220a or aptamers 220b in this embodiment) are coupled to the working electrode. In some embodiments, the aptamers 220b can be of the same type and can specifically bind to an epitope of a protein associated with a target pathogen. In other embodiments, the aptamers 220b can be of different types so that they bind to different epitopes of a pathogen's protein, e.g., some of the aptamers can specifically bind to one epitope of the pathogen's protein and some of the other aptamers can specifically bind to another epitope of that protein. By way of example, as discussed in more detail below, in some embodiments in which the electrochemical cell 216a is configured to detect SARS-CoV-2 virus, aptamer 220b can be selected so as to exhibit specific binding to one or more epitopes of the N or S proteins of the virus.

In some embodiments, the oligonucleotides coupled to the working electrode can have the same nucleotide sequence and hence can detect a single RNA or DNA segment of the target pathogen. In other embodiments, the oligonucleotides can include oligonucleotides with different nucleotide sequences so as to detect different RNA and/or DNA segments of the target pathogen.

Each of the electrochemical analysis cells functions by maintaining the electrical potential of the working electrode at a constant level relative to that of the reference electrode by adjusting the electrical current flowing through the counter electrode. The coupling of a protein and/or an RNA/DNA segment of a target pathogen to an aptamer or oligonucleotide coupled to the working electrode results in a change in the current flowing through the counter electrode, thereby generating a detection signal. As discussed in more detail below, in other embodiments, one or more of the electrochemical cells can be implemented as two electrodes having a plurality of interdigitated fingers. In such embodiments, the electrochemical cell does not include a reference electrode.

As noted above, the aptamers used to functionalize an electrochemical cell can be selected so as to exhibit specific binding to a protein of a target pathogen. In some other embodiments, the aptamers can be of different types, where each aptamer type exhibits specific binding to a different epitope of the protein of interest. For example, in some embodiments in which an electrochemical analysis cell is configured to detect SARS-CoV-2 virus, the aptamers can be selected to exhibit specific binding to N or S protein of the virus. In some embodiments, a sensor according to the present teachings can include one electrochemical analysis cell that is configured to detect the N protein (e.g., by employing aptamers that exhibit specific binding to one or more epitopes of the N protein) and another electrochemical analysis cell that is configured to detect the S protein (e.g., by employing aptamers that exhibit specific binding to one or more epitopes of the S protein).

As noted above, a sensor according to some embodiments can include, in addition to one or more sensing units that are configured to detect one or more proteins associated with a target pathogen, one or more sensing units that are configured to detect one or more RNA or DNA segments associated with the target pathogen. In some such embodiments, the nucleotide sequence of the oligonucleotide used to functionalize the electrochemical cell can be complementary to the nucleotide sequence of an RNA or DNA segment of a target pathogen. In some other embodiments, a plurality of oligonucleotides are attached to the working electrode, where the oligonucleotides exhibit oligonucleotide sequences that are complementary to different RNA or DNA segments of the target pathogen. By way of example, in some implementations, some of the oligonucleotides have a nucleotide sequence that is complementary to the nucleotide sequence of an RNA or DNA segment of the pathogen, and some of the oligonucleotides have a nucleotide sequence that is complementary to the nucleotide sequence of another RNA or DNA segment of the pathogen.

A variety of techniques can be employed for coupling aptamers and oligonucleotides to the working electrode of an electrochemical analysis cell. For example, in some embodiments in which the working electrode of an electrochemical analysis cell is formed of gold, the 5' terminal end of an aptamer exhibiting specific binding to a protein associated with a pathogen or an oligonucleotide exhibiting a complementary sequence relative to the RNA and/or DNA sequence associated with a target pathogen can be modified with a thiol SS-C6 group to enable thiol-gold binding to the gold surface of the working electrode. The modified aptamer or oligonucleotide can then be dissolved in a tris-HCl (TE) buffer (e.g., a 1 µM buffer) to generate a mixture that can be used to functionalize the working electrode. For example, the electrode surface can be coated with the mixture via drop coating. The coated electrode can then be incubated, e.g., for 30 minutes, before rinsing it with nuclease free water and drying it under a stream of inert argon gas to remove unbound aptamers and/or oligonucleotides.

In some embodiments, antibodies or nonobodies (generated in Llama), with high affinity to a target protein biomarker can be functionalized to one or more of the working electrodes of an electrochemical cell incorporated in a diagnostic device according to the present teaching. In some embodiments gold or carbon electrodes with self-assembled monolayers can be functionalized with a biotinylated antibody specific to the target of interest. The target is then detected with a matched antibody that is conjugated with HRP. The antibody pair can also be generated by Mega-STAR strategy with the matched antibody pairs presented on a single scaffold such as fibronectin type III domain (FN 3).

In some embodiments monobodies, generated via directed evolution methods, such as phase display technology, to exhibit high specific binding to an analyte (or an organism) of interest can be coupled, e.g., using the techniques discussed herein, to one or more of the working electrodes of an electrochemical cell incorporated in a diagnostic device according to the present teachings. By way of example, the monobodies described in an article entitled "Directed evolution of potent neutralizing nanobodies against SARS-CoV-2 using CDR-swapping mutagenesis," published in nature Biotechnology (doi: 10.1016/j.nbt), which is herein incorporated by reference in its entirety, can be used in some embodiments of the present teachings to functionalize at least one working electrode of an electrochemical cell of a sensor according to the present teachings for detecting SARS-CoV-2 virus. In this publication, the monobodies binding to the receptor binding domain of SARS-CoV-2 were identified. This was achieved by affinity selection from a phage library displaying $10^{10}$ monobody variants with a biotinylated fusion protein consisting of the spike RBD domain attached to the Fc region of human IgG1. Other monobodies used to detect other pathogens of interest via detecting an electrochemical signal generated by an electrochemical cell having a working electrode that is functionalized with a monobody exhibiting specific binding to a target pathogen, in response to specific binding the pathogen (or a constituent thereof) to the monobody.

As shown schematically in FIG. 3A, in some embodiments, the working electrode 301*a* of an electrochemical analysis cell 300 can be functionalized with a plurality of carbon nanotubes 302 to which a plurality of aptamer probes 303 are coupled. For example, the working electrode of a sensing unit that is configured to detect a target protein of interest can be functionalized with a plurality of carbon nanotubes that are themselves functionalized with one or more aptamers that exhibit specific binding to that target protein. Further, as shown schematically in FIG. 3B, the working electrode 301*b* of a another electrochemical analysis cell 300' that is configured to detect one or more RNA and/or DNA segments of a target pathogen can be functionalized with a plurality of carbon nanotubes 302 that are themselves functionalized with one or more oligonucleotides 304 that have a sequence complementary to the nucleotide sequence(s) of the DNA and/or RNA sequence. Once a target protein and/or a target RNA or DNA segment binds to the aptamer or the oligonucleotide, the electrochemical cell can generate a detection signal in a manner discussed above.

The functionalization of carbon nanotubes with one or more oligonucleotide probes and/or one or more nucleotide aptamer probes can be achieved using a variety of techniques known in the art. Some such methods rely on the formation of covalent bonds between the aptamer and oligonucleotide probes and the carbon nanotubes. For example, in some such embodiments, the carbon nanotubes can be carboxylated using known techniques and covalent bonds can be formed between the COOH groups of the carboxylated carbon nanotubes and the amine groups of the probes. In other embodiments, the carbon nanotubes can be functionalized using noncovalent via π-π interactions. For example, single-stranded DNA and RNA molecules with aromatic bases can be immobilized on the surfaces of carbon nanotubes via such interactions. Further details regarding various techniques for coupling aptamer and oligonucleotide probes to the surfaces of carbon nanotubes can be found, e.g., in an article entitled "Aptamer-functionalized carbon nanomaterials electrochemical sensors for detecting caner relevant biomolecules," published in Carbon 129 (2008) 380-395, which is herein incorporated by reference in its entirety.

The functionalization of gold electrodes with oligonucleotides, aptamers or with carbon nanotubes (CNTs) that are functionalized with oligonucleotides or aptamers can be achieved in some embodiments via direct self-assembly or via Chitosan.

For example, CNTs can be carboxylated via acid treatments in a manner known in the art. The negatively charged carboxyl groups on CNTs allow two approaches for direct self-assembly and immobilization of CNTs on electrode surfaces: one is the covalent bonding of CNTs to cysteamine self-assembled monolayer (SAM) modified gold electrodes via the reaction of carboxyl groups on CNTs and amino groups on cysteamine SAM in the presence of coupling reagents; the other is the attachment of CNTs to electrode surfaces via the electrostatic interactions between negatively charged carboxyl groups on CNTs and the positively charged species on the electrode surfaces. The self-assembly of CNTs on a gold electrode has been reported. In one such approach, as-grown carbon nanotubes were cut into short pipes and thiol-derivatized at their open ends by chemical methods. The ordered assembly of SWCNTs was then achieved by their spontaneous chemical adsorption to gold via Au—S bonds. Such an approach can result in the formation of a self-assembled monolayer of CNTs on gold with a perpendicular orientation. In contrast to the covalent methods for attaching CNTs to cysteamine modified gold electrodes, the attachment of acid-treated SWCNTs to cysteamine modified gold electrodes via electrostatic adsorption has also been reported. In addition, methods for preparing aligned CNT arrays on the surface of ordinary pyrolytic graphite (PG) electrodes from randomly dispersed CNTs by using a Nafion solution is also known.

As shown schematically in FIGS. 4A and 4B, in some embodiments, an electrochemical analysis cell 400*a*/400*b* according to the present teachings includes two interdigitated electrodes 402*a*/402*b*, each of which has a plurality of conductive fingers, where the fingers of the two electrodes are interleaved to form an interdigitated structure. One of the electrodes can function as the working electrode of the electrochemical analysis cell and the other electrode can function as the counter electrode. Without being limited to any particular theory, the close proximity of the fingers of the two electrodes (e.g., two adjacent fingers of the two electrodes can be separated by a distance, for example, in a range of about 5 microns to about 1 mm, though other distances can also be employed) can obviate the need for a reference electrode. The working electrode (i.e., the fingers of the working electrode) can be functionalized directly or via a plurality of carbon nanotubes in a manner discussed herein to allow detection of one or more proteins or one or more RNA/DNA segments of a target pathogen. For example, FIG. 4A schematically depicts a plurality of oligonucleotide probes 403 that are coupled to the surface of the working electrode and FIG. 4B schematically depicts a plurality of aptamer probes 405 that are coupled to the surface of the working electrode in a manner discussed herein.

In some embodiments, a heating element can be incorporated into an electrochemical cell according to the present teachings for heating, for example, the working electrode and hence the aptamer and/or oligonucleotide probes 504 coupled to the working electrode. For example, FIG. 5 schematically depicts a working electrode 500 of such an electrochemical cell that is deposited on an underlying substrate 501 (e.g., a glass, plastic, or other suitable substrates). A heating element 502 in the form of a resistive element is disposed below the substrate 501 to heat the substrate and the working electrode. In this embodiment, an electrical circuit 503 can apply a current to the resistive film to cause heating thereof. Such an electrical circuit can be implemented in a manner known in the art, e.g., by implementing a current source. By way of example, the heating element can be used to heat the working electrode to a temperature in a range of about 60° C. to about 65° C. Without being limited to any particular theory, in some embodiments, such heating can advantageously disentangle those aptamers and/or oligonucleotides that have been entangled, e.g., due to close proximity and the natural molecular motion of the probes, thereby allowing a more facile interaction of the probes with target proteins and/or RNA/DNA segments of a pathogen. A control unit (not shown) can control the operation of the heating element, for example, for activating the heating element for a selected time period followed by deactivating the heating element.

In some embodiments, commercial electrochemical sensors can be obtained and modified in accordance with the present teachings, e.g., to functionalize one of their electrodes with aptamer or oligonucleotide probes. By way of example, electrochemical sensors marketed by Metrohm DropSens of Ovieda, Spain can be employed in some implementation of a sensor according to the present teachings.

Figure 6:
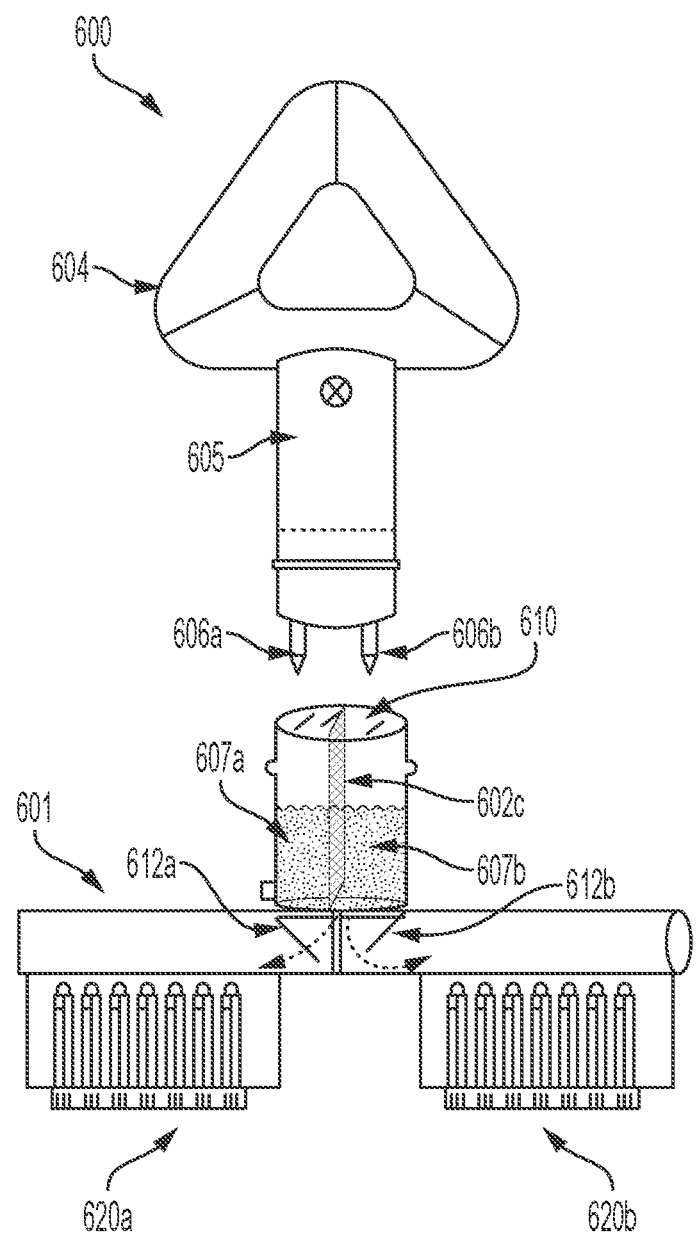
FIG. 6 schematically depicts another embodiment of a system according to the present teachings for detecting pathogens, where the system includes a sensor having two reservoirs for storing sample-processing reagents for preparing a sample for the detection of one or more pathogen proteins or one or more pathogen RNA and/or DNA segments.

FIG. 6 schematically depicts a system 600 according to the present teachings, which is similar to the sensor 100, except that it includes two reservoirs that are separated by a partition that can be formed, e.g., of a polymeric material (such as PDMS). The top openings of the two reservoirs is sealed by a thin polymeric layer. By way of example, the thin polymeric layer can be formed of soft polyurethane, or other suitable polymers.

Similar to the previous embodiment, the system 600 includes a mouth/nose piece 604 and a tube 605 that is connected to the mouth/nose piece 604 to receive breath samples collected by the mouth/nose piece. The system 600 further includes a sensor 601, which includes a conduit 603 having a proximal end 603a that can be coupled to the distal end of the tube 605 so as to engage the mouth-nose piece 604 with the sensor 601.

In this embodiment, two reservoirs 607a/607b separated by a partition 607c are disposed within the chamber 603. A frangible membrane 610 (such as a polymeric layer) covers the inlets of the two reservoirs 607a/607b. At outlets of the two reservoirs 607a/607b, two flapper valves 612a/612b are disposed.

In this embodiment, two prongs 606a/606b extend from the distal end of the tube 605, where each prong provides a conduit for delivering a portion of the breath samples into one of the two reservoirs 607a/607b. More specifically, upon coupling of the distal portion of the tube 605 with the proximal end of the chamber 603, the distal ends of the prongs 606a/606b puncture the portions of the frangible membrane 610 sealing the reservoirs 602a/602b, thereby allowing a portion of the breath samples to be mixed with the reagents stored in the reservoir 602a and another portion of the breath samples to be mixed with the reagents stored in the reservoir 602b. By way of example, in one of the reservoirs (e.g., reservoir 607a) a viral transport medium together with reagents for processing the sample for protein detection is stored, and in the other reservoir (e.g., reservoir 607b) a viral transport medium together with reagents for processing the sample for RNA/DNA detection is stored. The actuation of the flapper valves 612a/612b via an actuator (e.g., a mechanical actuator (not shown in this figure) allows the processed samples from the reservoirs 607a/607b to be delivered, respectively, to a plurality of sensing units 620a and 620b, wherein the sensing units 620a are configured in a manner discussed herein for detection of one or more viral proteins of a target pathogen and the sensing units 620b are configured in a manner discussed herein for the detection of one or more RNA/DNA segments of the target pathogen.

The distal end of the tube 605 can be configured to allow puncturing the two portions of the frangible membrane sealing the two reservoirs without damaging the partition that separates the two reservoirs. For example a surface portion 622 of the distal end can have a concave profile to allow penetration of the two prongs in the two reservoirs via puncturing the seal without the surface portion of the distal tube between the two prongs exerting excessive pressure on the partition, which may damage the partition 607c separating the two reservoirs.

In some embodiments, the reagents stored in the chamber 607a for processing a portion of a received sample to facilitate the detection of at least one protein of a target pathogen, when present in the sample, can include either (1) sodium dodecyl sulphate (SDS) at a final concentration of 0.2%; (2) a final concentration of 0.1%-1% Triton X-100, or (3) 0.1% Tween 20 added to VTM to inactivate the virus and maintain the target viral protein intact. In some such embodiments, the reagents stored in the chamber 607b for processing the sample to facilitate cell lysis and viral nucleic acid (e.g., RNA and/or DNA) stabilization and detection can include the reagents stored in the chamber 607a with the addition of guanidine isothiocyanate (e.g., 2M final concentration).

In both cases, PBS (potassium-buffered saline) or HBSS (Hank's balanced salt solution) can be used as the buffer. Anti-microbial (e.g., gentamicin) and anti-fungal (e.g., amphotericin B) can be optionally added to each chamber of the reservoir, although in many cases the use of such ani-microbial and anti-fungal agents may be not be needed because of the short temporal interval between sample collection and testing. In some embodiments, phenol red can be added to the sample for visual observation of the sample, and in particular to verify the pH of the sample (Phenol red exhibits a pink or red color at neutral or basic pH and transitions to yellow at acidic pH).

The separation of the protein buffer and RNA/DNA buffer can provide certain advantages. For example, in some cases, a buffer that is effective in preparing a sample for detection of one or more proteins of a target pathogen can adversely affect the RNA and/or DNA of that pathogen, or vice versa. For example, as noted above, Guanidinium Thiocyanate can be added to the buffer in chamber 607b as a lysis and nucleic acid stabilization buffer. Guanidium Thiocyanate, however, can disrupt protein structures. Thus, the separation/isolation of the reagents for preparing the sample for protein detection and RNA/DNA detection into two separate chambers mitigates, and preferably eliminates, the potential for adverse effect of the reagents suitable for one type of sample processing on another type of sample processing.

Further, the use of two different buffers can lead to more consistent test results. For example, when a test result indicates the presence of a target RNA/DNA segment, but the absence of a target protein, one can eliminate the possibility that the adverse effect of a buffer on the target protein has led to an anomalous result.

In some embodiments, one or more sensing units of a sensor according to the present teachings can be configured to detect one or more antibodies produced by an individual in response to infection by a pathogen (e.g., IgG, IgA and/or IgM antibodies). For example, in some such embodiments, a viral protein to which the IgG, IgA and/or IgM antibodies exhibit specific binding can be used to functionalize the working electrode of an electrochemical analysis cell. Such a sensing unit can then be employed to detect IgG, IgA and/or IgM antibodies in an individual's serum. In some embodiments, a sensor according to the present teachings can include multiple sensing units, where one or more sensing units are configured to detect one or more proteins associated with a target pathogen, one or more sensing units are configured to detect one or more RNA/DNA segments associated with that pathogen, and one or more sensing units are configured to detect one or more antibodies (e.g., IgG, IgA and/or IgM antibodies) produced by a patient's immune system in response to the infection caused by that pathogen.

In a related aspect, a sensor according to the present teachings, such as those discussed above, can be used with sample collection devices other those configured for the collection of breath samples. Such sample-collection devices include, without limitation, devices for collecting saliva, and nasopharyngeal samples. A sample collected in such a manner can then be delivered into a sensor according to the present teachings. By way of example, such a sample can be introduced into the sensor 601 depicted in FIG. 6. More specifically, a portion of the sample can be introduced into the chamber 607a and another portion of the sample can be introduced into the chamber 607b and the sensor can be employed to determine whether one or more proteins associated with the target pathogen and/or more RNA and/or DNA segments associated with that target pathogen are present in the sample.

Figure 7:
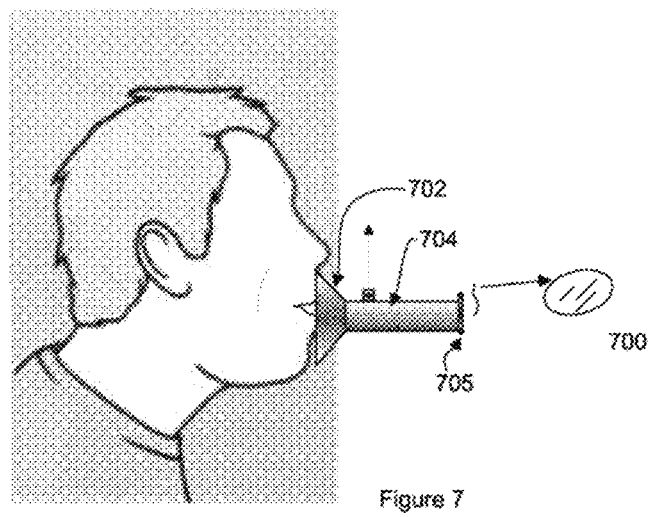
FIG. 7 schematically depicts a saliva collection device that can be coupled to a sensor according to the present teachings for detecting a target pathogen in the collected saliva.

By way of example, FIG. 7 schematically depicts a sample collection device 700 for collecting a saliva sample. The sample collection device 700 includes a mouth piece 702 that is connected to a tube 704 at a proximal end thereof. The tube 704 can engage at it distal end with a sensor according to the present teachings, such as the sensor 200 discussed above (See, e.g., FIG. 1A). An O-ring 705 disposed in the distal portion of the tube 704 can engage with a groove provided in proximity of an inlet of the sensor to provide a seal between the collection device 700 and the sensor.

Similar to the previous embodiment, the engagement of the sample collection device 700 with the sensor results in the puncture of a seal associated with one (and more generally two) reservoirs in which sample-processing reagents are stored. A user can then spit into the mouthpiece and the salvia will flow into the sensor via the tube 704. In this embodiment, the sample collection device 700 can optionally include a valve 706 to which a syringe (not shown) can be coupled to deliver a liquid (e.g., a saline solution) into the tube for facilitating the transfer of the saliva into the sensor.

In other embodiments, a sensor according to the present teachings can be employed to test environmental samples (e.g., air and/or water samples) for the presence of one or more target pathogens. By way of example, the samples can be collected using known collection techniques and subsequently be introduced into a sensor according to the present teachings, such as the above sensor 100, to determine whether the samples contain one or more target pathogens. In some cases, such testing can be used for the identification and/or surveillance of environmental "hot spots."

In other embodiments, a sensor according to the present teachings can be employed to detect one or more target pathogens in blood. By way of example, a sensor according to the present teachings can be configured to detect HIV (human immunodeficiency virus) via the detection or at least one protein and at least one RNA segment of the virus.

In some embodiments, a sensing unit configured via functionalization with one or more oligonucleotide probes to detect one or more RNA/DNA sequences of a target pathogen can generate a detection signal even in absence of a complete complementarity between the probe sequence of a target RNA/DNA segment of the pathogen. For example, in some embodiments, such a sensing unit can generate a detection signal when a single nucleotide polymorphism (SNP) is present in the target RNA/DNA segment of interest.

Figure 8A:
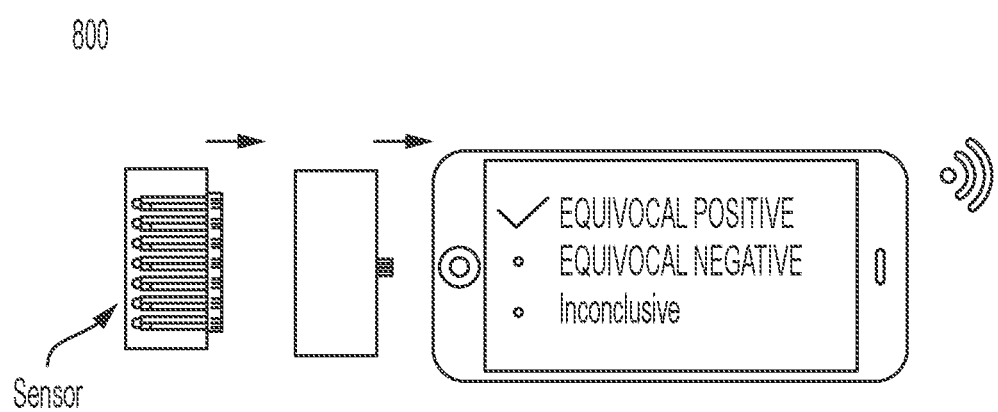
FIG. 8A schematically depicts an analysis module for processing data generated by a sensor according to the present teachings.

FIG. 8A schematically depicts an analyzer 800 according to an embodiment, which can receive data from a sensor according to the present teachings and process that data to indicate whether a target pathogen is present in a sample. For example, when at least one protein-detecting sensing unit of a sensor indicates that presence of at least one protein of a target pathogen in the sample, and at least one RNA/DNA detecting sensing unit of the sensor indicates the presence of at least one RNA and/or DNA segment associated with the target pathogen, the analyzer can provide an indication, e.g., via textual and/or graphical means, that the target pathogen is present in the sample. The analyzer can also employ other criteria, e.g., more stringent criteria, for indicating that a target pathogen is present in a sample under study. For example, the analyzer may be configured to indicate the presence of a pathogen in the sample when at least one protein and at least two RNA and/or DNA segments are found in a sample.

By way of example, the analyzer 800 can indicate whether the test result is positive (i.e., the target pathogen is present in the sample), it is negative (i.e., the target pathogen is not present in the sample), or the test result is inconclusive. The negative indication can be provided when none of the one or more target proteins and the one or more target RNA/DNA sequences are detected. The inconclusive indication may be provided, for example, when at least one target protein is detected without the detection of any of the target RNA/DNA segments, or vice versa.

Figure 8B:
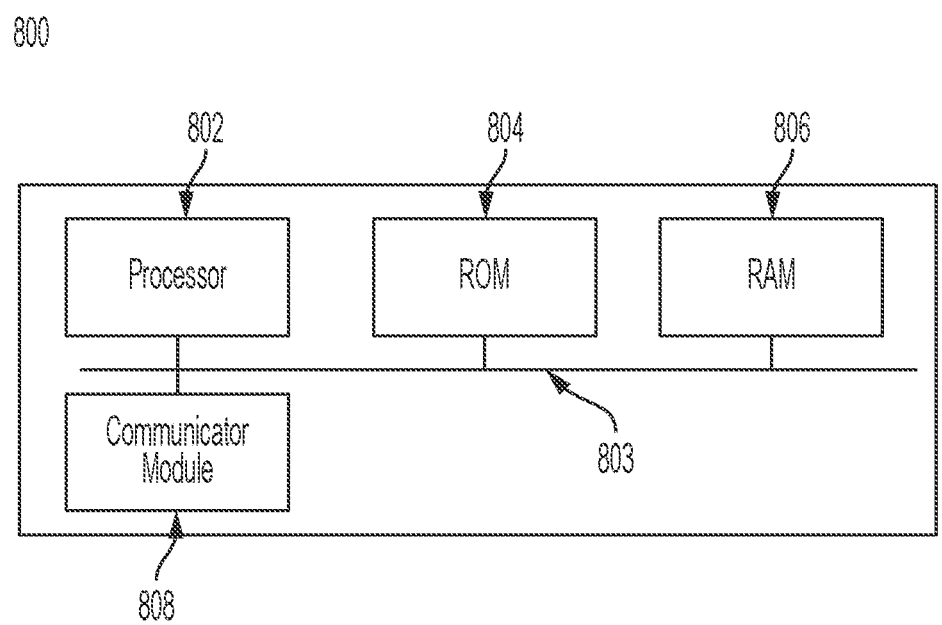
FIG. 8B schematically depicts an example of the implementation of the analysis module depicted in FIG. 8A.

The analyzer 800 can be implemented in hardware, software and/or firmware in a manner known in the art informed by the present teachings. For example, FIG. 8B schematically depicts such an implementation of the analyzer, which includes a processor 802, at least one random access memory module (RAM) 804, at least one permanent memory module (ROM) 806, a communication module 808 (e.g., a wireless communication module using any of the known protocols). The processor 802 can communicate with the other components of the analyzer via a communication bus 803. The instructions for analyzing the data received from a sensor can be stored in the ROM module 804 and be transferred into the RAM module 806 by processor for execution.

In some embodiments, at least one sensing unit of a sensor according to the present teachings is configured to provide a negative control. By way of example, one sensing unit can be functionalized with aptamers for detecting actin protein.

Without any loss of generality, in some embodiments, a system according to the present teachings can be configured to detect SARS-CoV-2 virus in a sample. SARS-CoV-2 virus has multiple structural proteins including the Spike (S), Nucleocapsid (N), Envelope (E), Membrane (M) proteins. Several studies have demonstrated that N protein is a good diagnostic biomarker. For example, during the outbreak of SARS-CoV-2, it was demonstrated that the N protein can be detected very early, as early as day 1, during infection in various patient samples including blood, nasopharyngeal aspirate, urine, and fecal samples. It was also demonstrated that N-protein detection can achieve a very high sensitivity of 90% positive.

Additionally, the receptor binding domain (RBD) of S protein is thought to be another key diagnostic target.

SARS-CoV2 infects human respiratory epithelial cells using angiotensin-converting enzyme (II) (ACE2) through the (RBD) of S protein.

By way of example, such a system can include one or more sensors that are configured, via coupling of oligonucleotides to the working electrode of an electrochemical analysis cell, to detect one or more RNA sequence(s) of the virus and one or more sensors that are configured, via coupling of aptamers to the working electrode of an electrochemical analysis cell, to detect one or more proteins of the virus.

In some embodiments, the secondary structure of a nucleic acid segment (e.g., an RNA segment), such as hairpins, can be determined, e.g., theoretically using techniques known in the art, in order to identify the nucleotides that are exposed and can be utilized for the identification of that nucleic acid segment.

By way of example, in some embodiments of the present teachings, in order to identify target sequences in the RNA genome of coronaviruses that include accessible regions, UNAFold Software developed by Markham and Zuker at SUNY Albany and licensed by Integrated DNA Technology can be used to identify and avoid hairpin and secondary structures.

By way of example, primers listed in the table depicted in FIG. 17 were designed for Spike, Nucleocapsid, M protein and ORFlab for SARS-CoV-2 virus were BLAST searched to show 100% identity with their designated gene and have specificity against OC43, 229E, NL63, MERS, and SARS1 coronaviruses as well as the human genome. The guanine-cytosine (GC) content of the primers were considered to ensure that the GCs are distributed evenly in order to avoid hairpin and self-binding.

In this example, the primers were optimized for binding with high affinity at RT-37 C. These primers can detect complementary sequences with up to 3 nucleic acid changes, potentially allowing the detection of close variants of SARS-CoV-2.

As shown in FIG. 17, in order to minimize degradation of the nucleic acids of a primer by exonucleases and endonucleases, modified nucleic acids can be used in the primer design. For example, in some embodiments, (A) 2' O-methyl chemical modifications can be employed to make the primers that are stable against endonucleases; and (B) 3' phosphorothioate linkages are used to block exonuclease degradation.

As noted above, in some embodiments, a sensor according to the present teachings is configured to detect highly homologous regions of coronaviruses, e.g., proteins that exhibit high homology regions. The generation of a positive detection signal by such a sensor, in response to interrogation of a sample, for the highly homologous region but negative detection signals for some or all of a plurality of other regions that do not exhibit such high homology between the different family members of the coronavirus can lead to the conclusion that it is likely that the sample contains an emergent variant (i.e., a novel strain) of the coronavirus. A similar approach can be employed for detecting the emergent variants of other pathogens (e.g., other viruses).

In some embodiments, in order to validate the functionality of a biosensor according to the present teachings, synthetic non-infectious RNA genomes can be used as an alternative to the live virus and as an alternative to plasmids containing viral sequences. For example, the binding and selectivity of biosensors designed to detect SARS-CoV-2 unique sequences can be validated using synthetic non-infectious SARS-CoV-2 RNA. In comparison to a plasmid with incorporated RNA genome, the use of synthetic RNA genomes for validating a biosensor according to the present teachings has the advantage that they contain the secondary structures and hairpins associated with respective viral RNA segments, and thereby only biosensors and recognition elements that bind to the accessible regions of will be chosen. Additionally, as compared with the natural genomic RNA, these synthetic RNAs are non-infectious.

In some embodiments, linkers such as 5' ThioMc6-D, can be added to 3' or 5' ends of such primers for coupling of the primers onto electrodes (or other surfaces) of the sensing units (e.g., aforementioned electrochemical cells) through S—S bonds.

By way of further illustration, FIG. 18 presents sequences of examples of aptamers for detecting the Nucleocapsid and/or Spike proteins of SARS-CoV-2 virus.

A system according to the present teachings that can provide multiplexed detection of at least one protein and/or at least one genetic component of a pathogen can be implemented in a variety of different ways for detecting a pathogen in a variety of different biological specimens.

With reference to FIGS. 19A-19D, a disposable cartridge 4000 according to an embodiment of the present teachings, which includes three layers 4002 (bottom layer), 4003 (middle layer), and 4004 (top layer) that are assembled to collectively form a cartridge frame. In this embodiment, the top and bottom layers are formed of optically transparent materials, e.g., glass or an optically clear polymeric material. In some embodiments in which the top layer is formed of glass, the inner surface of the glass may be coated with a polymeric coating (e.g., a coating of PDMS) at least in areas of the inner glass surface that may come into contact with portions of a sample under analysis. In some such embodiments, the entire inner coating of a top glass layer may be coated with a layer of a suitable polymeric coating. By way of example, FIG. 19B shows PDMS layer 4023 that coats the inner layer of the upper glass layer 4004. This allows inhibiting the direct contact of specimens and/or processing buffers disposed in various reservoirs (wells) provided in the middle layer.

In this embodiment, the middle layer is formed of a polymeric material, e.g., PDMS, in which wells (reservoirs, chambers) as well as microfluidic channels are formed, as discussed in more detail below.

The above three layers can be assembled using fabrication techniques known in the art as informed by the present teachings. By way of example, as noted above, a thin layer of PDMS can be deposited on an inner surface of the upper glass layer, e.g., via a liquid polymer cast, and the polymeric layer can then be sandwiched between the two glass layers.

In this embodiment, the middle layer includes a sample-receiving well 4005 that can receive, via an inlet port 4007, a sample for analysis. The cartridge 4000 can be configured for analysis of a variety of different biological specimens. In general, the cartridge 4000 can be configured for diagnostic analysis of liquid biopsy samples. Some examples of samples that can be analyzed using the cartridge 4000 include, without limitation, blood and saliva.

The cartridge 4000 further includes two wells (reservoirs) 4008/4009 in one of which a buffer for processing (preparing) a portion of the received sample for detection of one or more target genetic components of a target pathogen, when present in the received sample, is stored (herein referred to for brevity as the "genetic buffer)) and in the other a buffer for processing (preparing) another portion of the received sample for detection of one or more target proteins of the target pathogen is stored (herein referred to for brevity as the "protein buffer"). For ease of description, it is assumed that in this embodiment, the well 4008 stores the genetic buffer and the well 4009 stores the protein buffer.

A fluid channel 4011*a* fluidly connects the sample-receiving well 4005 to the buffer well 4008 and another fluidic channel 4011*b* fluidly connects the sample-receiving well to the buffer well 4009. A isolation valve 4013 inhibits the backflow.

Figure 19A:
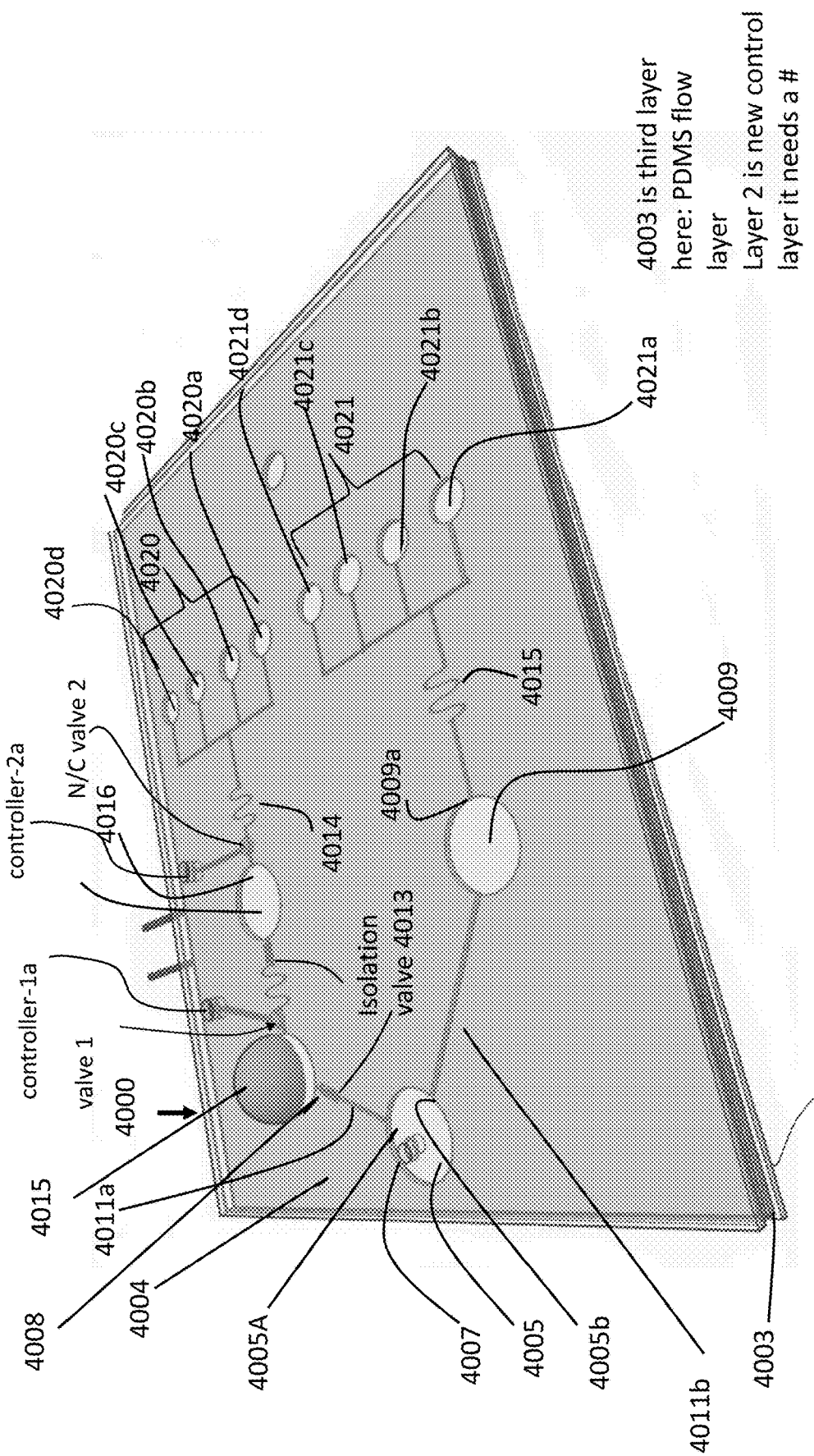
FIG. 19A schematically depicts a disposable cartridge according to an embodiment of the present teachings.

The sample portions received in the reservoirs 4008/4009 come into contact with the genetic and protein buffers, respectively. With particular reference to FIGS. 19A and 19C, in this embodiment, the buffer reservoir 4008 is in the form of a blister pouch 4015 in which the genetic buffer is stored. The blister pouch 4015 includes a flexible membrane 4015*a* forming an enclosure within which the buffer is stored. A separation membrane 4015*b* is disposed within the blister pouch over an internal puncture arm 4015*c*. The blister pouch can be activated to cause the liquid stored within the pouch to be released by pressing on the flexible membrane 4015*a* such that the increase in the liquid pressure within the blister's enclosure can cause the crushing of the internal puncture arm, via pressure exerted thereon by the separation membrane 4015*b*, thereby releasing the liquid from the pouch.

In this embodiment, a pneumatically-controlled valve 1 coupled to the blister pouch 4015, and controlled via a controller 1*a*, facilitates the transfer of the liquid released from the blister pouch 4015 to a downstream amplification reservoir (well) 4016 for amplifying genetic components (DNA/RNA) in the liquid released from the blister pouch associated with a target pathogen, when that target pathogen is present in a sample collected from a subject. The amplification of the genetic components can be achieved using a variety of different amplification modalities. For example, in some embodiments, isothermal amplification methods can be used while in others amplification methods that require temperature cycling can be employed.

By way of example, in this embodiment, the amplification well 4016 can contain one or more reagents (such as primers) suitable for performing isothermal amplification of DNA/RNA extracted from a target pathogen, when that pathogen is present in the sample. By way of example, a genetic buffer contained in the buffer reservoir can include, among other reagents, a reagent for lysing a target pathogen so as to release one or more RNA/DNA segments of that pathogen. Such RNA/DNA segments can then undergo isothermal amplification in the amplification well.

Figure 19B:
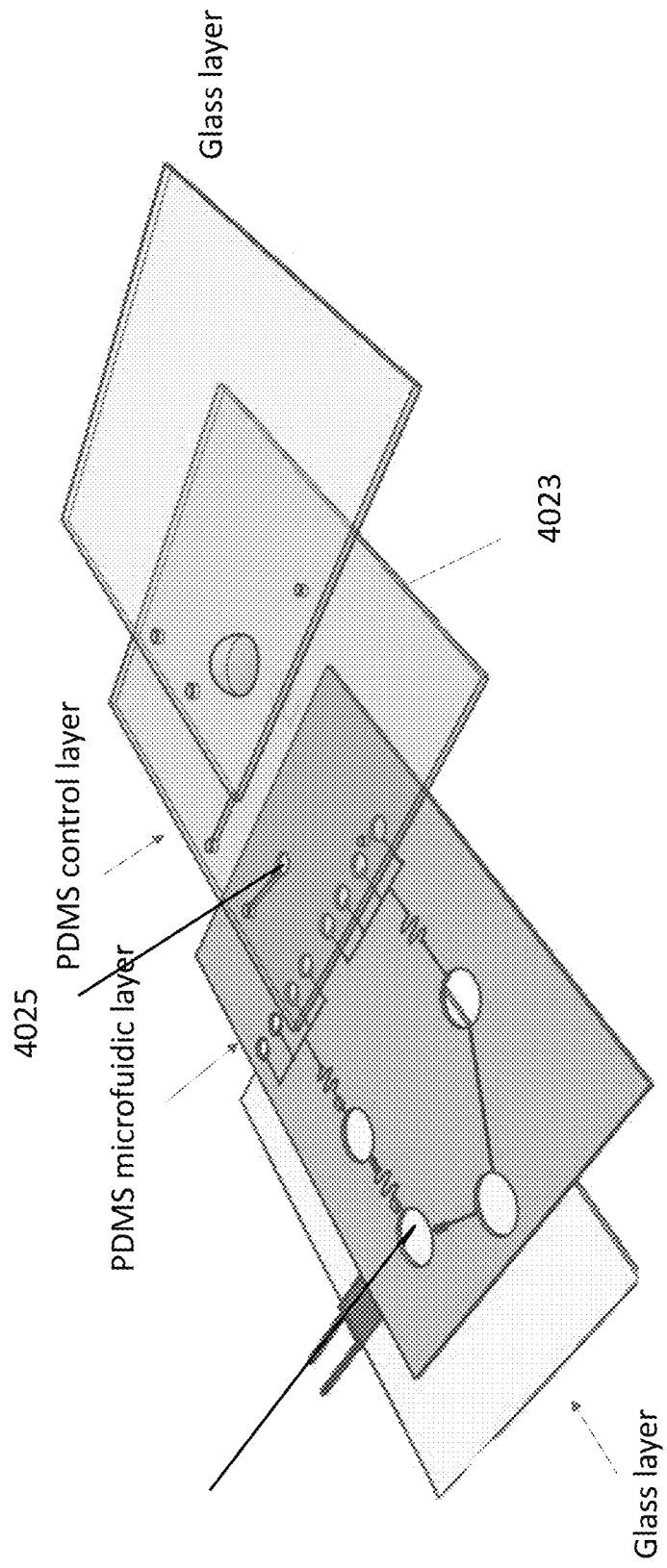
FIG. 19B is an exploded schematic view of the cartridge illustrated in FIG. 19A.
Figure 19C:
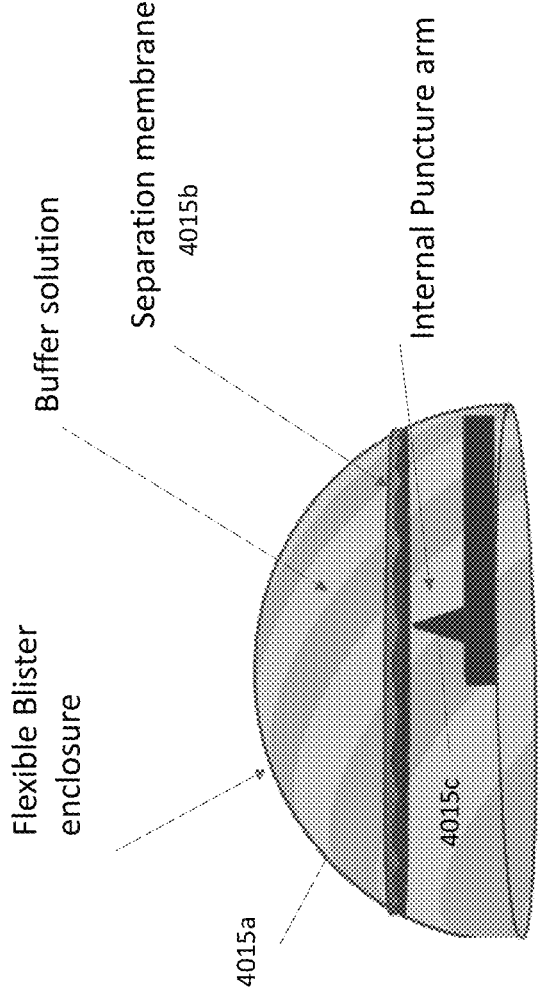
FIG. 19C schematically depicts a blister pouch incorporated in the disposable cartridge depicted in FIGS. 19A and 19A for storing a buffer and functioning as a pump for releasing the buffer for introduction to a downstream amplification reservoir.
Figure 19D:
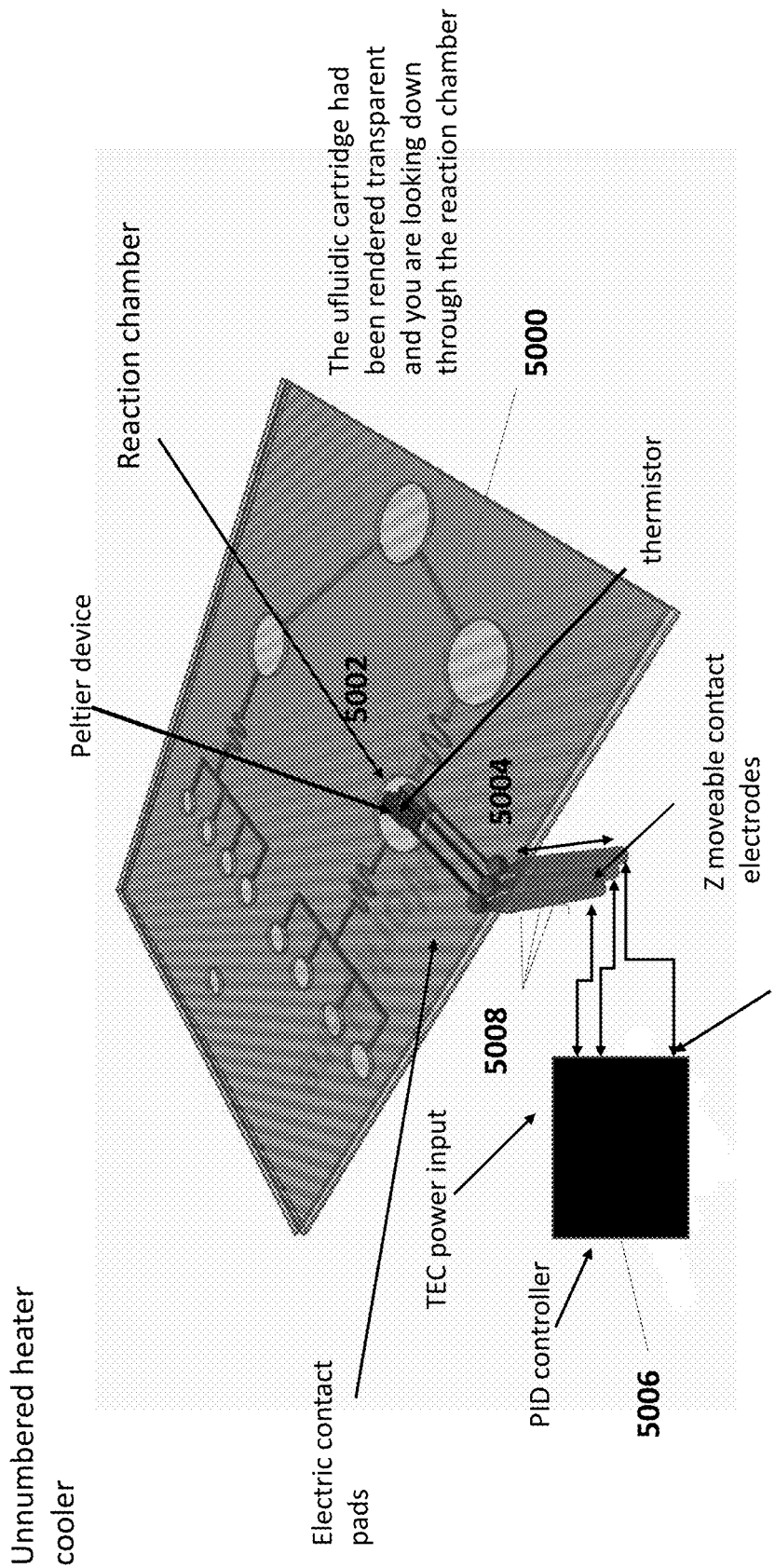
FIG. 19D schematically depicts the cartridge shown in FIGS. 19A and 19B as well as a heating/cooling device employed for regulating the temperature of a liquid within an amplification reservoir, and a controller disposed in a console that receives the cartridge.

With particular reference to FIG. 19D, in this embodiment, a heating/cooling element 5000 in the form of a Peltier device and its associated thermistor 5002, which are incorporated in the cartridge for controlling the temperature of a sample received in the amplification well 4015. For example, the Peltier device and the thermistor (which may be incorporated into the Peltier device) can be thermally bonded to the bottom layer of the cartridge under the amplification well (reservoir).

In this embodiment, a plurality of electrical contact pads 5004 allow electrically connecting the Peltier device and the thermister to a thermoelectric controller (TEC) 5006 provided in a console that is configured for receiving the cartridge 4000, as discussed in more detail below.

More specifically, upon insertion of the cartridge 4000 into the console, a plurality of movable, spring-biased, electrodes 5008 (in the shape of rods) can electrically connect the Peltier device to the PID controller and further allow the controller to receive a temperature readout from the thermister. In this embodiment, the controller 5006, which can be implemented as a PID controller, can provide electrical power to the Peltier device and regulate the supplied power to ensure that the temperature of a sample within the amplification well 4016 remains at a desired temperature (e.g., for isothermal amplification) or is cycled between two or more temperatures (e.g., for PCR amplification).

The controller can receive a signal from the thermistor that is indicative of the measured temperature of the liquid within the amplification well and can compare that temperature with a desired value (or range), and adjust the power supplied to the Peltier device based on that comparison. In some embodiments, the controller can be programmed to cycle the temperature of the liquid within the amplification well between two or more temperatures via controlling the Peltier device, e.g., such that the device provide heating and cooling cycles and/or different heating cycles.

After amplification of the genetic components, if any, are completed, the pneumatically-controlled valve 2 can be activated via its associated controller 2*a* to transfer the amplified sample, via passage through a mixing element 4014 that is implemented as a serpentine channel, to a bank of sensors 4020, each of which is configured to detect a different genetic component of the target pathogen (e.g., different RNA and/or DNA segments of the target pathogen). The passage of the sample through the mixing element 4014 further facilitates the preparation of the sample for detection of the target genetic components, if any, therein. For ease of description, the liquid exiting the mixing element is herein referred to as a processed sample.

More specifically, in this embodiment, the bank of detecting elements 4020 includes four sensors 4020*a*, 4020*b*, 4020*c*, and 4020*d*, each of which is configured to detect a different target genetic component (e.g., RNA and/or DNA strands) associated with a pathogen of interest. By way of example, in some implementations, each of the detecting elements 4020 can be implemented as an electrochemical sensor functionalized for detection of a target genetic component (i.e., a target oligonucleotide), in a manner discussed above.

With particular reference to FIG. 19A, in this embodiment, the protein buffer reservoir 4009 is fluidly connected to the sample-receiving reservoir 4005 to receive a portion of a sample collected from an individual via a fluidic channel 4011*b*. The interaction of the received sample portion with the protein buffer can generate a processed sample suitable for introduction into a bank of detectors 4021 for detection a plurality of proteins associated with the target pathogen, when present in the sample collected from the subject. More specifically, in this embodiment, the bank of detecting elements 4021 includes four sensors 4021*a*, 4021*b*, 4021*c*, and 4021*d*, each of which is configured to detect a different target protein associated with the pathogen of interest. For example, in this embodiment, each of the detecting elements can be implemented as an electrochemical sensor functionalized for detection of a different target protein, in a manner discussed above.

Although the above cartridge 4000 includes an amplification well, other cartridges according to the present teachings may not rely on amplification of genetic components of a target pathogen for detection thereof in a biological specimen. For example, some such cartridges may lack the amplification well 4016 and the associated devices and circuitry, such as those discussed above, for performing the amplification of one or more genetic components associated with a target pathogen, when present in a sample.

Figure 20:
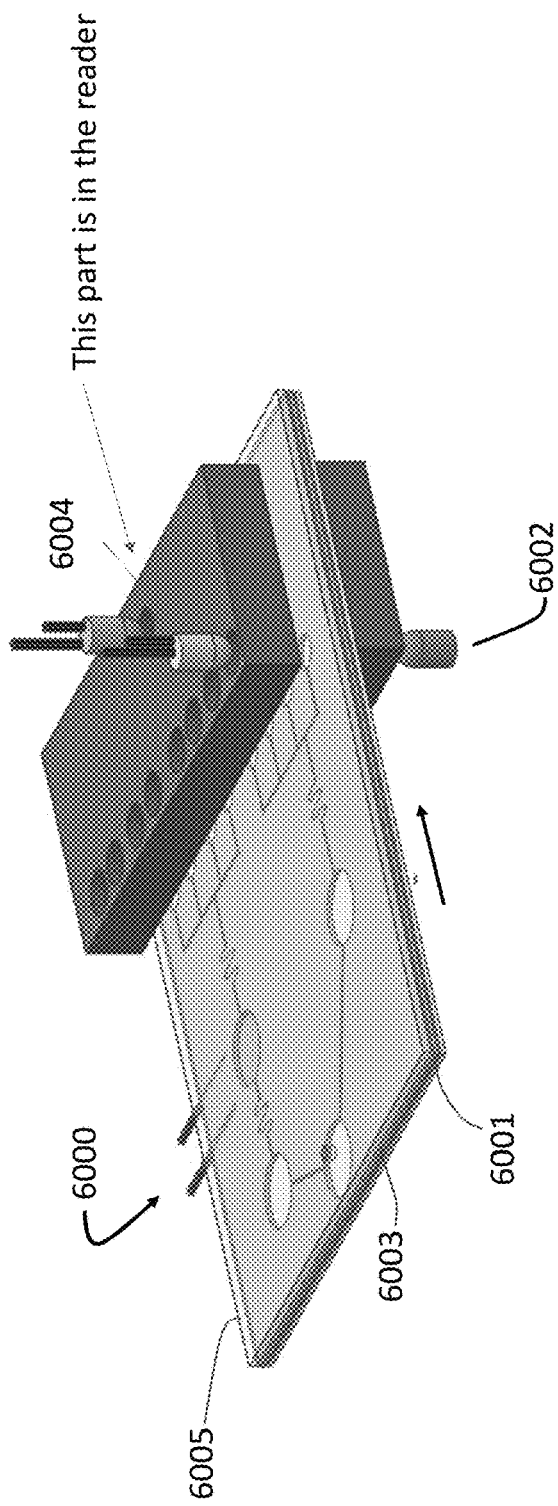
FIG. 20 is a schematic view of a cartridge according to another embodiment, which is configured for optical analysis of a biological sample.

In other embodiments, in addition to or instead of electrochemical detection, one or more of the detecting elements may be configured for optical detection of a target protein and/or genetic component. By way of illustration, FIG. 20 shows an embodiment 6000 of a disposable cassette according to the present teachings, which employs optical techniques for interrogating a processed sample for detection of one or more target pathogens, when present in the sample. By way of example, an optical source 6002 (e.g., a laser diode) positioned in a console (herein also referred to as a reader), which is further discussed below and into which the cartridge 6000 can be inserted, can illuminate a sample received within one or more wells (e.g., the detecting elements 4020 and/or 4021 can be replaced with wells each of which can receive a processed sample that can be optically interrogated).

In this example, the optical source 6002 is positioned below a lower transparent layer 6001 of the cartridge to illuminate the sample and a detector 6004 is positioned above the upper transparent layer 6005 to receive at least a portion of the radiation passing through one or more wells provided in the middle polymeric layer 6003. By way of example, in some embodiments, a sample can be processed to attach Raman tags to a target protein of a pathogen of interest, e.g., by providing Raman tags in a buffer reservoir, and the radiation source 6002 can be configured to generate radiation having a wavelength suitable for exciting Raman mode(s) of the tag. In such an embodiment, the detector 6004 can detect any of the Stokes and/or anti-Stokes Raman scattered radiation. Other modes of optical detection of the target protein and/or the target genetic component, such as fluorescence, absorption, can also be employed. The term "optical radiation" is used herein broadly to refer to radiation having a wavelength in a range from UV (e.g., about 200 nm) to the infrared portion of the electromagnetic spectrum.

With reference to FIG. 19B, the cartridge 4000 further includes a background reference well 4025, which can be used to obtain the effect of the optical radiation passing through the lower and the upper glass layers in order to obtain a baseline for analysis of the optical radiation detected after passage through a sample well.

Figure 21B:
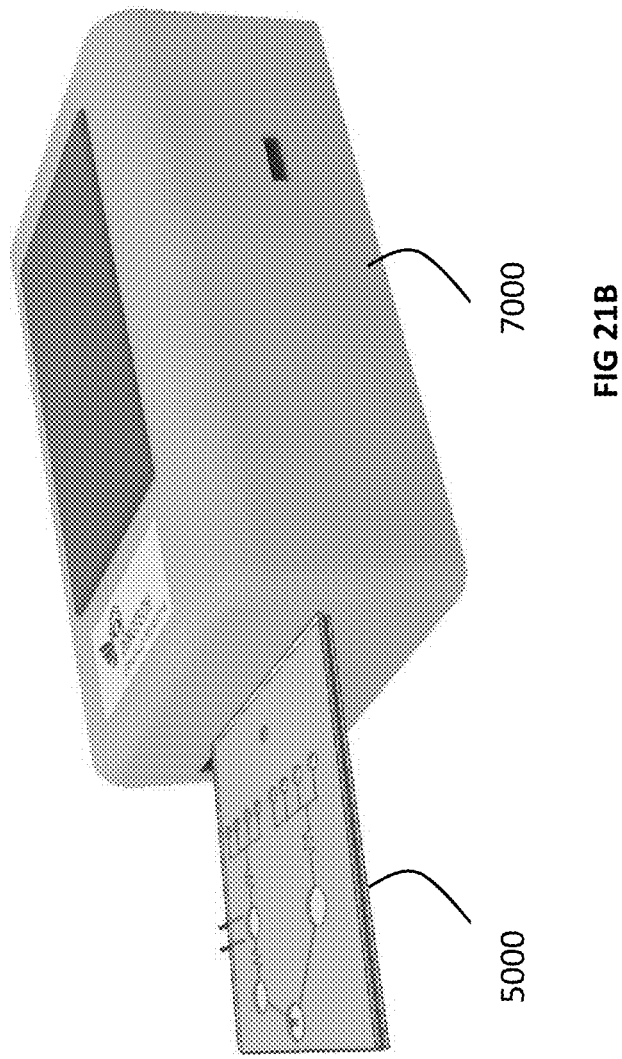
FIG. 21B is another schematic view of the diagnostic system depicted in FIG. 21A, illustrating how the cartridge can be inserted into the console.
Figure 21C:
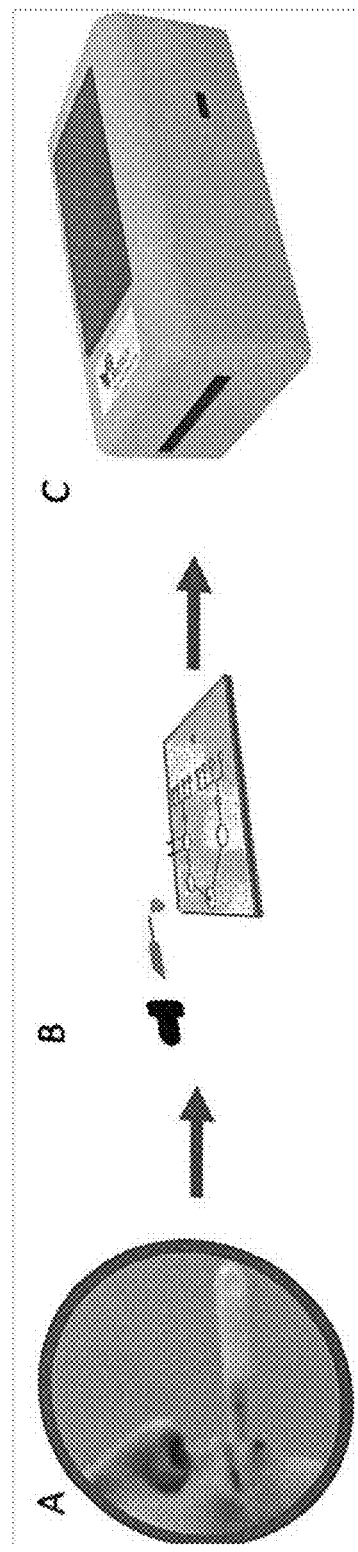
FIG. 21C schematically depicts that in use a biological sample can be introduced into the cartridge and the cartridge can be inserted into the console for analysis of the received sample.

With reference to FIGS. 21A-21C, a system for detecting a pathogen according to the present teachings can include, in addition to a disposable cartridge (e.g., the cartridge 4000 depicted in the figure), a console (reader) 7000, that can receive the cartridge to interrogate samples collected from a subject, e.g., as discussed above, and/or receive, process and analyze signals generated by the sensors incorporated in the cartridge and/or perform other functions required for determining whether one or more target pathogens are present in a collected biological specimen. Such functions can be implemented, e.g., in a manner discussed above in connection with the previous embodiments using techniques known in the art as informed by the present teachings. In this embodiment, the console 7000 includes a receptacle 7002 into which the cartridge can be inserted.

With particular reference to FIGS. 21B and 21C, in use, a biological specimen (e.g., a saliva sample) can be collected from a subject and be introduced into a cartridge according to the present teachings (e.g., any of the above cartridges) via the inlet port of the cartridge. The cartridge can then be inserted into the console 7000. The console 7000 can include mechanisms for actuating various valves, pumps, etc. incorporated in the cartridge, e.g., according to a predefined temporal schedule to process a received sample in a manner discussed above. The console can also be programmed to analyze the data received via various sensors incorporated in the cartridge and/or the console to determine whether a target pathogen is present in a collected biological specimen above a limit-of-detection (LOD) associated with the system.

For example, similar to the above embodiments, in some cases, if a system according to the present teachings detects at least one protein and at least one genetic component associated with a target pathogen, the system will confirm the presence of the target pathogen in the sample. It should be understood that other algorithms for confirming the presence of the target pathogen can also be employed based on the signals generated by the sensors. For example, one such algorithm may require that a plurality of proteins and a plurality of genetic components associated with a target pathogen be detected for confirmation of the presence of the target pathogen in the collected sample.

The controller can include software/firmware that can operate the various pumps and valve of the cartridge, e.g., according to a predefined sequence. For example, a pneumatic plunger can puncture the blister pouch to introduce the buffer to the amplification well. And the heating/cooling element can be operated to provide amplification of one or more genetic components of the sample. After a predefined amplification cycles (e.g., 10 cycles), the valve 2 can be actuated via it controller to introduce the amplified sample into the bank of sensors 4020. The instructions for such sequential activation/operation of the valve and the pumps can be stored in a memory module and be accessed during runt-time via a processor to perform the requisite actions.

Figure 22:
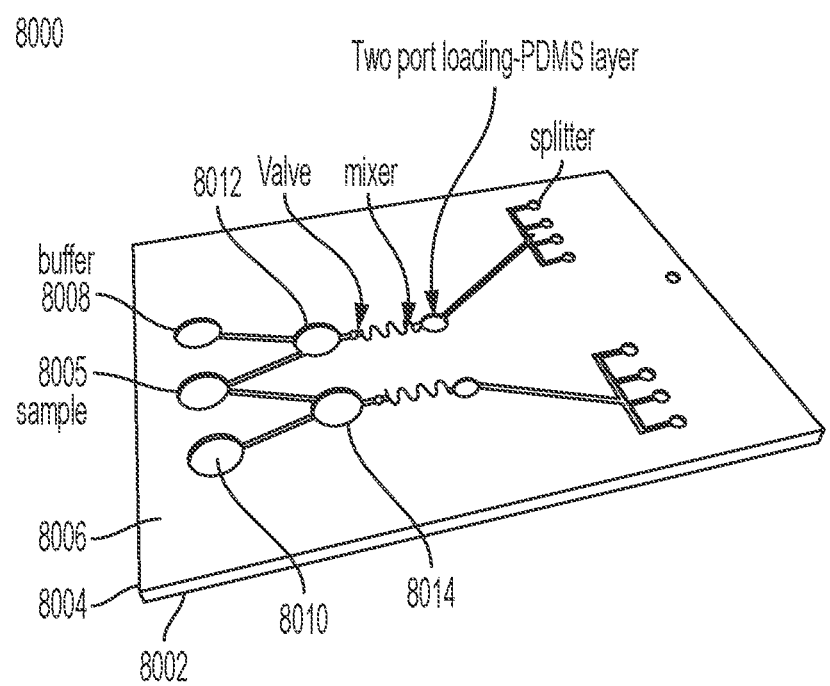
FIG. 22 is a schematic view of a disposable cartridge in accordance with another embodiment of the present teachings.

With reference to FIG. 22, in some embodiments, another cartridge 8000 according to the present teachings can be implemented using three layers 8002, 8004, and 8006, where the upper and lower layers are formed of an optically transparent material, such as glass (e.g., glass coated with a suitable polymer) and the middle layer is formed of a suitable polymeric material (e.g., PDMS). Similar to the previous embodiments, the cartridge 8000 includes an inlet for introducing a biological specimen into a sample-receiving reservoir 8005 and two buffer reservoirs 8008/8010 containing, respectively, a genetic buffer and a protein buffer. Unlike the previous embodiments, in this cartridge, a collected sample is not transferred directly to the buffer reservoirs. Rather, the cartridge 8000 includes two sample-processing wells 8012/8014 that are both in fluid communication with the sample-receiving reservoir 8005 for receiving portions of the collected sample.

The sample-processing well 8012 is in fluid communication with the genetic buffer reservoir 8008 while the sample-processing well 8014 is in fluid communication with the buffer reservoir 8010. Various valves and pumps (e.g., such as those discussed above) can regulate the release of the sample and the buffers from the respective wells/reservoirs and facilitate their introduction into the sample-processing wells 8012/8014 for interacting with the sample portions introduced into those wells. In some embodiments, the use of such sample-processing wells can advantageously allow storing a larger volume of a buffer in any of the buffer reservoirs. Similar to the previous embodiments, the cartridge 8000 includes two banks of sensors 8016/8018, where the sensors 8016 are configured for detecting one or more proteins of a target pathogen and/or proteins associated with a plurality of different target pathogens and the sensors 8018 are configured for detecting one or more genetic components of a target pathogen and/or genetic components associated with a plurality of different target pathogens. The sample-processing wells 8012 and 8014 are in fluid communication with mixers 8020/8022, respectively, which cause the mixing of processed samples released from the sample-processing wells for transfer to the sensors. A pair of valves 8026/8028 regulate the release of the processed samples from the sample-processing wells 8012/8014, respectively.

In some embodiments, in addition to or instead of detecting one or more constituents (e.g., proteins and/or genetic components) of a pathogen to determine whether that pathogen is present in a biological specimen, one or more sensors incorporated in a system according to the present teachings can be configured to detect the intact pathogen, when present in the sample at a level greater than the limit-of-detection (LOD) of the sensor. By way of example, such a sensor can include an electrochemical sensor having a working electrode that is functionalized with an antibody (or other suitable affinity binding elements) that exhibit specific binding to the target pathogen. For instance, some pathogens such as coronaviruses have many Spike proteins coating their surface, thereby the virus in its entirety may be captured by affinity binding elements to Spike, (i.e, specific antibodies, monobodies, nanobodies). By way of further illustration, such an electrochemical sensor can be functionalized with a monobody that is generated via phase display technology to exhibit specific binding to a pathogen of interest. For example, as discussed above, monobodies described in the above article entitled "Directed evolution of potent neutralizing nanobodies against SARS-CoV-2 using CDR-swapping mutagenesis," published in nature Biotechnology (doi: 10.1016/j.nbt), which is herein incorporated by reference in its entirety.

Detection of Emergent Pathogens

In one aspect, the present teachings can be employed to detect emergent pathogens, e.g., a new form of SARS-CoV virus. For example, when a sample under investigation in accordance with the present teachings contains one or more proteins associated with known variants of SARS-CoV but none of the target RNA sequences associated with such viruses, one can conclude that the sample is likely to contain a new variant of SARS-CoV virus. For example, Non-structural proteins (nsps) of coronaviruses are highly conserved components of the coronavirus life cycle as well as the life cycle of other emerging RNA viruses. RNA-dependent RNA polymerase (RdRP), also known as nsp12, replicates the viral RNA genome and generates viral RNA transcripts. RdRp is essential for virus function and is unique to viruses and not present in the host, thus exhibits no cross-reactivity. Due to a high homology among RdRp of SARS-CoV viruses, the detection of such a protein indicates the presence of a virus in this viral family. However, the absence of one or more of the structural proteins and the unique RNA segments associated with known SARS-CoV viruses can be an indication that the detected virus is a new variant of the SARS-CoV family. In other words, the detection of RdPP coupled with lack of detection of the unique RNA segments associated with known SARS-CoV viruses can indicate that the sample is likely to contain an emergent SARS-CoV variant.

The detection of one or mor proteins associated with a pathogen (e.g., a virus) without the detection of signal indicative of the presence of a single RNA/DNA segment associated with that pathogen may be in fact indicate the detection of a mutant form of the pathogen, rather than the detection of an emergent pathogen in that family. However, the detection of one or more proteins associated with a pathogen without the detection of signals corresponding to two or more RNA/DNA segments associated with that pathogen increases the likelihood that the sample includes an emergent pathogen in that family, rather than a mutant version of that pathogen. This is so because the probability that multiple mutations occur concurrently decreases rapidly as the number of those mutations increases.

In one aspect, the present teachings can be employed to detect emergent pathogens, e.g., a new form of SARS-CoV virus. For example, when a sample under investigation in accordance with the present teachings contains one or more proteins associated with known variants of SARS-CoV but none of the target RNA sequences associated with such viruses, one can conclude that the sample is likely to contain a new variant of SARS-CoV virus. For example, Non-structural proteins (nsps) of coronaviruses are highly conserved components of the coronavirus life cycle as well as the life cycle of other emerging RNA viruses. RNA-dependent RNA polymerase (RdRP), also known as nsp12, replicates the viral RNA genome and generates viral RNA transcripts. RdRp is essential for virus function and is unique to viruses and not present in the host, thus no cross-reactivity. Due to a high homology among RdRp of SARS-CoV viruses, the detection of such a protein indicates the presence of a virus in this viral family. However, the absence of one or more of the structural proteins and the unique RNA segments associated with known SARS-CoV viruses can be an indication that the detected virus is a new variant of the SARS-CoV family.

In some embodiments, a sensing electrode of an electrochemical sensing unit according to one aspect of the present teachings can be functionalized with a plurality of nanoparticles, which are in turn functionalized with an affinity binding element that is configured to exhibit specific binding to a target analyte (e.g., a target pathogen). By way of example, in some embodiments, nanoparticles can be substantially spherical with a diameter in a range of about 5 nm to about 100 nm, e.g., in a range of about 10 nm to about 50 nm, or in a range of about 20 nm to about 30 nm, though other sizes can also be employed. By way of example, the nanoparticles can be formed of gold.

FIG. 9 schematically depicts an example of such a functionalized sensing electrode 900 that includes an underlying gold layer 901 and a plurality of gold nanoparticles 902 that are distributed over the gold layer 901.

The gold nanoparticles 902 can in turn be functionalized with a plurality of affinity binding elements 904. By way of example, the gold nanoparticles can be functionalized with affinity binding elements that exhibit specific binding to a target protein or a target genetic component (e.g., an RNA segment), e.g., a viral protein or a viral RNA segment. In some embodiments, the affinity binding elements 904 can also include at least one ligand that can facilitate anchoring, e.g., via covalent bonds, the gold nanoparticles to the underlying gold layer. An example of such coupling ligand can be a thiol group, e.g., a cysteine group. In some embodiments, an affinity binding element of interest can be thiolated to allow its coupling to the underlying gold layer.

A variety of techniques for the synthesis of gold nanoparticles (AuNPs) are known. By way of example, colloidal AuNPs can be prepared as follows: 0.5 mL of 1% (w/v) sodium citrate solution can be added to 50 mL of 0.01% (w/v) HAuCl4 boiling solution. HAuC14 and sodium citrate aqueous solutions can be filtered through a 0.22 μm microporous membrane filter before using. The mixture can be boiled for 15 minutes and then stirred for 15 minutes after removing the heating source to produce colloidal gold nanoparticles. The mixture can be stored in a refrigerator in a dark-colored glass bottle before using.

In some embodiments, commercially available gold nanoparticles, such as those marketed by Nanopartz of Loveland Colo., USA can be employed. By way of example, some such gold particles can have pentahedrally—faceted profiles and can have diameters in a range of 60 nm to 100 nm with size accuracies better than 5 nm and size variances less than 10%. They exhibits peak SPRs (surface plasmon resonances) in a range of 780 nm to 980 nm.

As noted above, the gold nanoparticles can be anchored to the underlying gold surface using a variety of ligands. For example, cysteine ligands can be used to immobilize AuNPs to the underlying gold surface. In one method of functionalizing an underlying gold surface with a plurality of AuNPs, the gold surface can be cleaned, e.g., via exposure to a plasma. In other embodiments, the cleaning of the gold surface can be achieved via polishing the surface with an abrasive paper, followed by rinsing the surface with ethanol and distilled water and then drying the surface with filter paper. The cleaned gold surface can then be immersed in a cysteine aqueous solution (e.g., a 0.1 M cysteine aqueous solution) for a few hours, e.g., for 2 hours, at room temperature in darkness. The resulting modified electrode can then be rinsed thoroughly with distilled water and soaked in distilled water for 12 hours in order to remove any physically-adsorbed cysteine. The cysteine-functionalized gold surface can then be dipped into the colloidal gold solution for 24 hours at 4° C. The AuNPs self-assembled electrode can be dipped into distilled water for conservation at 4° C.

Further details regarding synthesis and functionalization of a gold surface with functionalized gold nanoparticles are provided in an article entitled "Single Layer of Gold Nanoparticles Self-Assembled on Gold Electrode as a Novel Sensor with High Electrocatalytic Activity," published in Journal of Analytical Chemistry, 2018, Vol. 73, No. 11, pp. 1118-1127. © Pleiades Publishing, Ltd., 2018, which is herein incorporated by reference in its entirety.

In some embodiments, an affinity binding element (e.g., an aptamer or other oligonucleotides) of interest with which a sensing electrode of a detector according to the present teachings is functionalized can include ligands (e.g., thiol groups) that allow coupling the affinity binding element to the sensing electrode. In other cases, an affinity binding element can be chemically modified to include ligands (e.g., thiol groups) that would facilitate its attachment to the working electrode.

The functionalization of a sensing electrode of an electrochemical sensing unit can advantageously increase the effective surface area of the sensor, thereby enhancing the sensitivity of the sensor for the detection of an antigen of interest.

In some embodiments, a detection system according to an embodiment of the present teachings can include, in addition to one or more sensors having one or more electrochemical sensing units, at least one sensing unit that employs surface enhanced Raman spectroscopy (SERS) for the detection of a protein, an RNA or a DNA segment of a target pathogen.

In some such embodiments, a sensing electrode can function as an electrochemical sensor and can also provide a surface suitable for performing surface enhanced Raman spectroscopy. By way of example, the gold nanoparticle functionalized gold layer depicted schematically in FIG. 9 can provide such dual sensing functionality.

For example, in some such embodiments, the electrode 900 can be used in a manner discussed above as an electrochemical sensing unit to generate an electrical signal in response to the coupling of an antigen of interest, when present in a sample under investigation, to the affinity binding element coupled to the electrode surface. The electrode 900 can also be used as a SERS surface to allow interrogation of the sample via Raman spectroscopy. In some embodiments, the gold nanoparticles can have sizes, e.g., in a range of about 6 nm to about 100 nm, though other sizes can also be employed.

By way of example, in this embodiment, the electrode 900 is functionalized with human cellular receptor angiotestin-converting enzyme 2 (ACE2). The recognition and binding of receptor binding domain (RBD) of SARS-COV-2 spike protein by the ACE2 enzyme can result in a change in electrical conductivity of the electrode 900, which can be detected in a manner discussed above in connection with the previous embodiments.

In addition, the binding of the spike protein to the ACE2 enzyme can cause changes in the Raman spectrum of the ACE2 enzyme, thereby providing a biomarker (a signature) for Raman detection of SARS-COV-2 virus. For example, the ACE2 enzyme coupled to the gold nanoparticles in absence of coupling to the spike protein can exhibit the following SERS signals: 1032, 1051, 1089, 1189, 1447 and 1527 $cm^{-1}$.

The binding of SARS-CoV-2 protein to the ACE2 enzyme can lead to substantial decrease in the intensities of most of these peaks and a red-shift of the 1189 $cm^{-1}$ peak to 1182 $cm^{-1}$. Such changes in the Raman spectrum can then be used as a signature for detecting the presence of SARS-CoV-2 virus in a sample.

In some embodiments, the ratio of Raman intensity at 1182 $cm^{-1}$ to that at 1189 $cm^{-1}$ can be used as a diagnostic measure for the detection of SARS-CoV-2 virus in a sample under study. In addition or alternatively, multivariate analysis of the Raman data can be employed as a tool for determining whether SARS-CoV-2 virus is present in a sample under investigation. For example, principal component analysis (PCA) of the Raman data can be used to reduce the dimensionality of the data. The primary principal components can then be processed using linear discriminate analysis (LDA) to classify the data into classes corresponding to the presence or absence of the virus in the sample under investigation.

Figure 10:
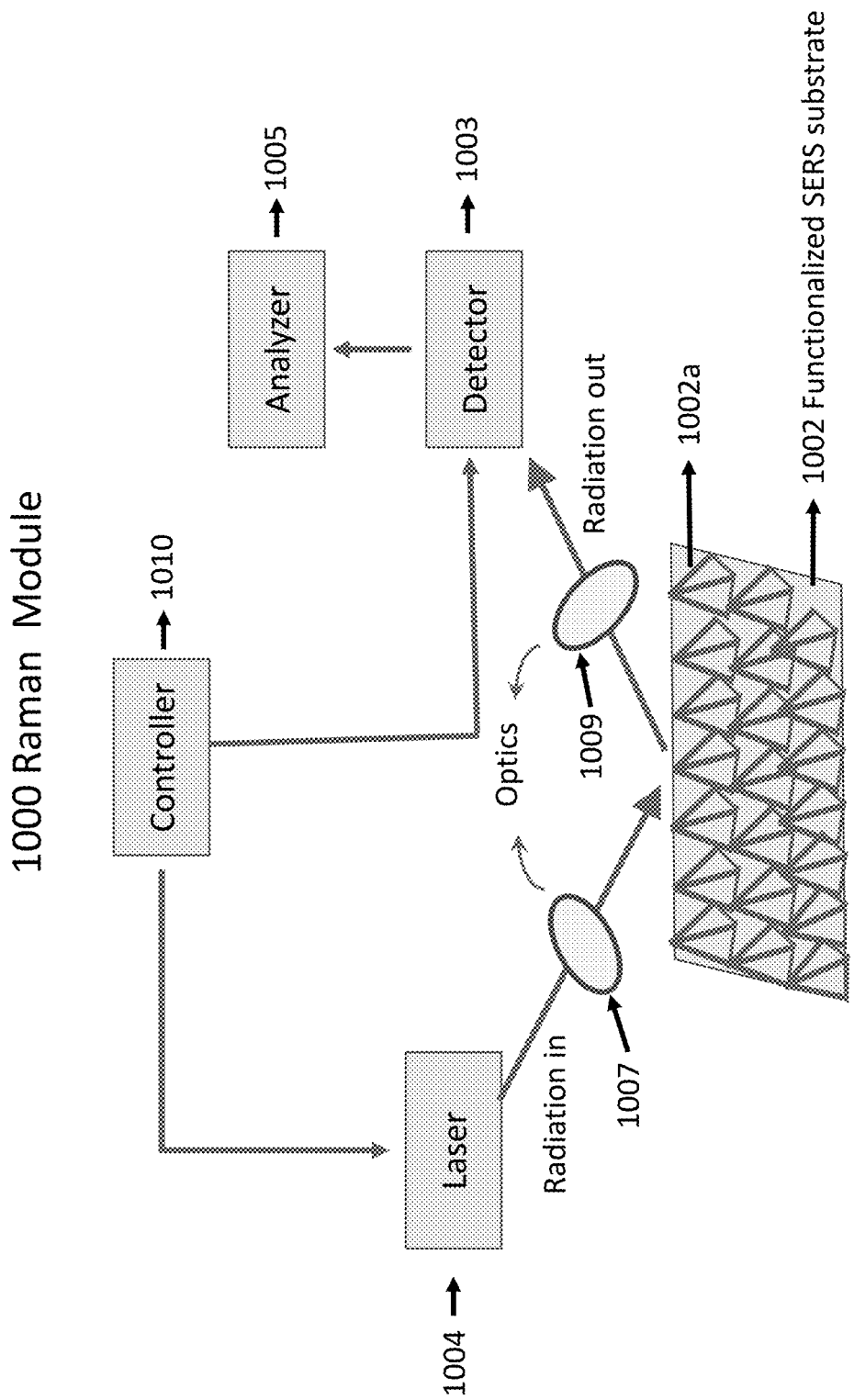
FIG. 10 schematically depicts a SERS module suitable for use in some embodiments of the present teachings.
Figure 11:
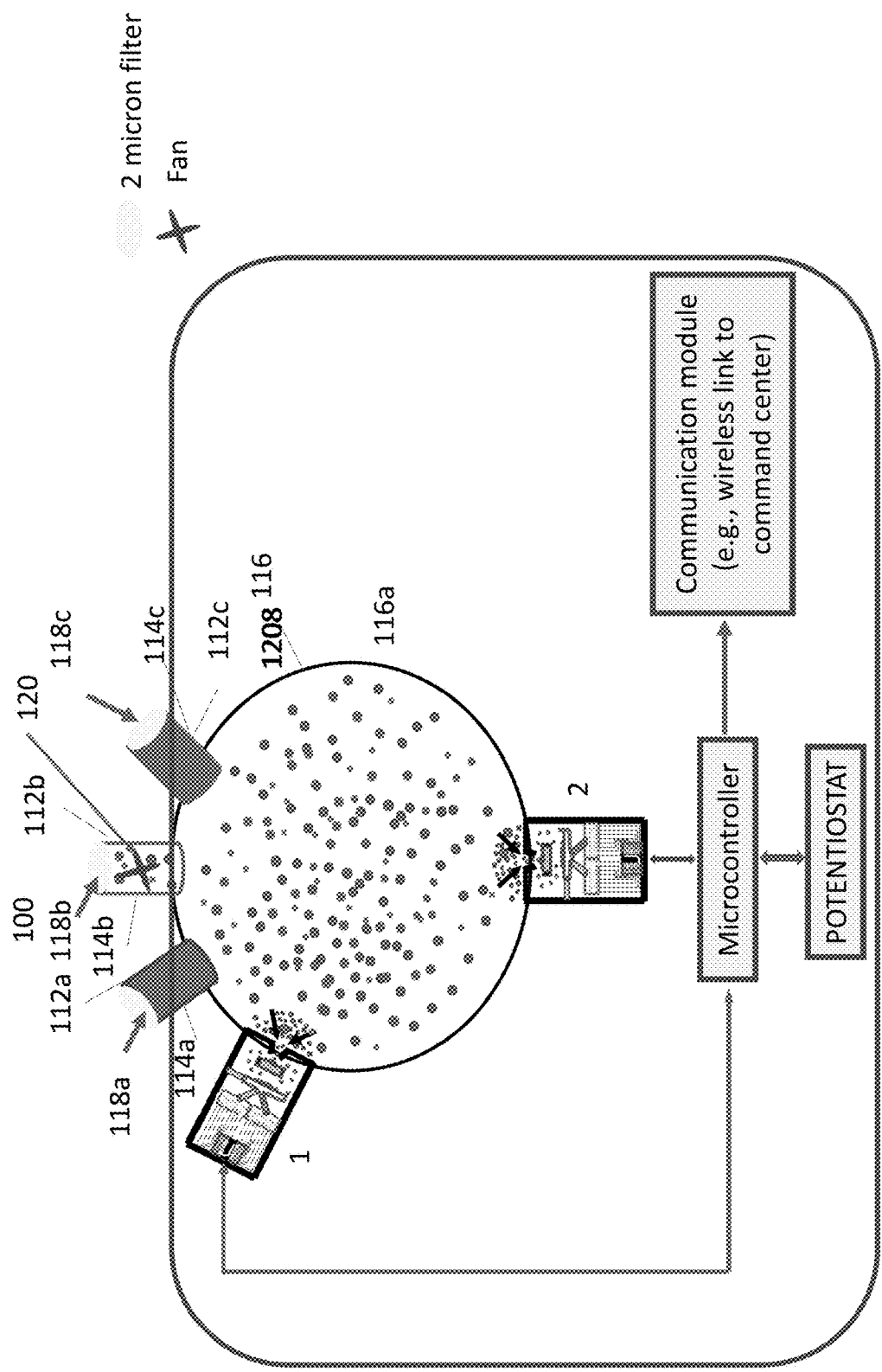
FIG. 11 schematically depicts an air monitoring system according to an embodiment of the present teachings.
Figure 12:
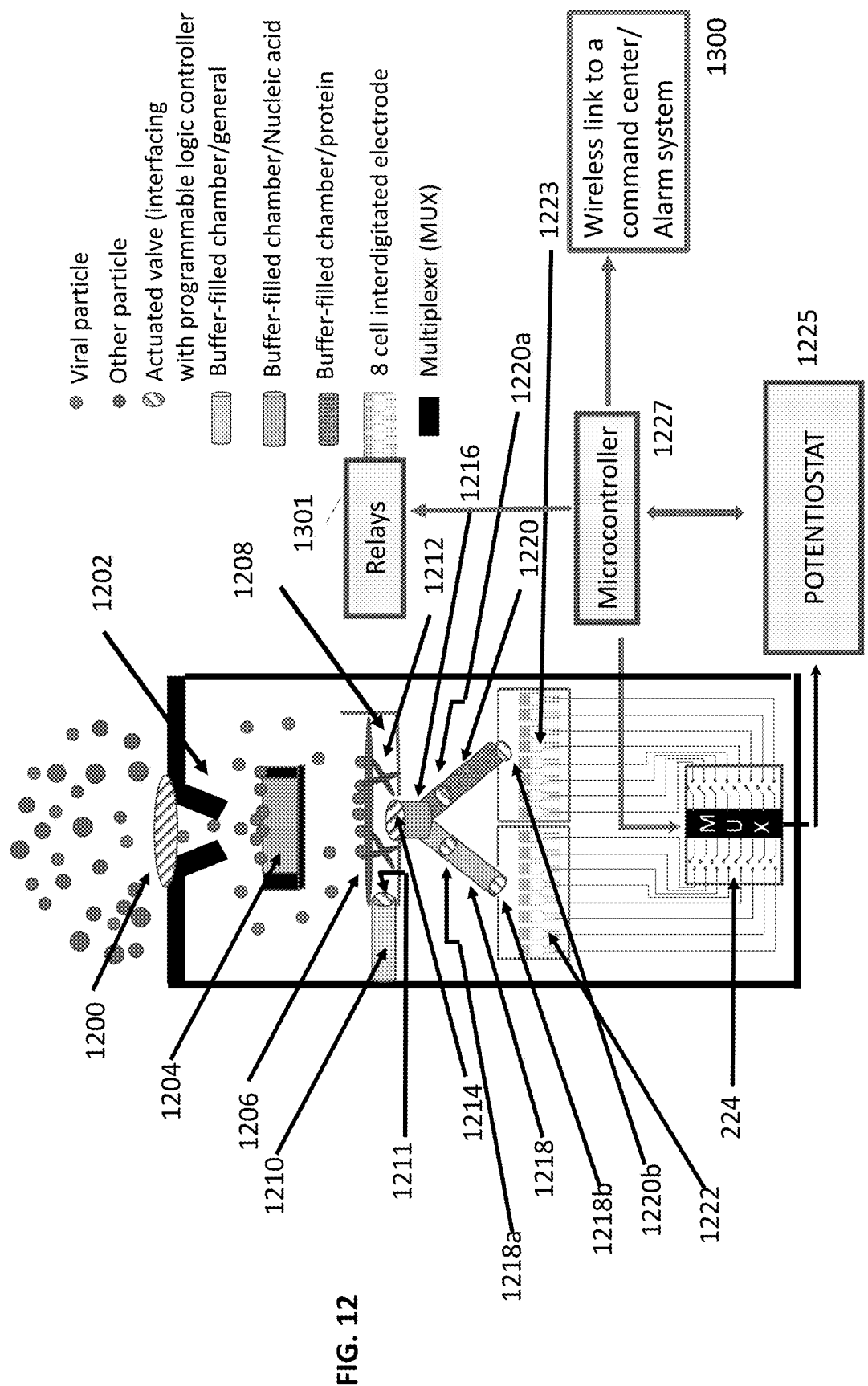
FIG. 12 schematically depicts a sensing unit used in the air monitoring system depicted in FIG. 11.
Figure 14:
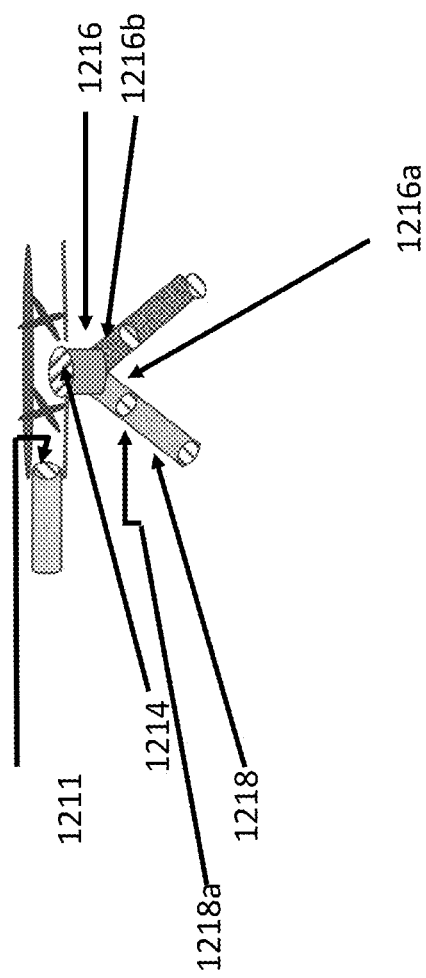
FIG. 14 schematically depicts a portion of the sensing unit shown in FIG. 12.
Figure 15:
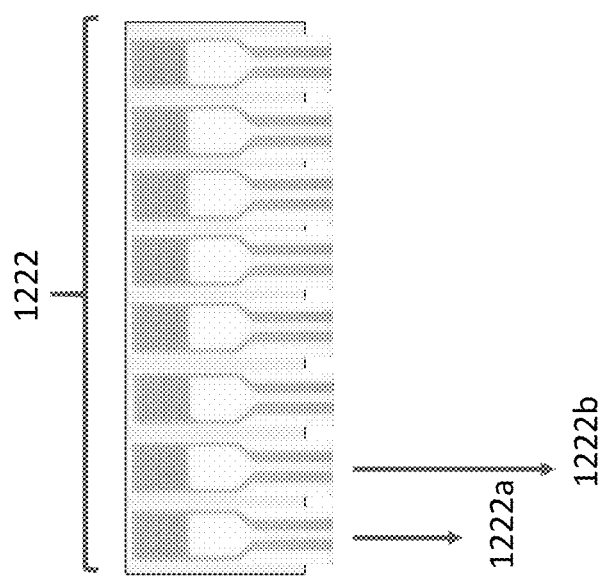
FIG. 15 schematically depicts a plurality of sensing modules associated with the sensing unit shown in FIG. 12.

In some embodiments, a system according to the present teachings can include a SERS module that is separate from the electrochemical sensing modules. In other words, in some such embodiments, the SERS module can be employed only for obtaining SERS data. By way of example and with reference to FIG. 10, such a SERS module 1000 can include a SERS surface 1002 that includes a plurality of metalized protrusions/corrugations 1002a.

The surface 1002 can be functionalized with an affinity binding element that can provide specific binding to an antigen of interest. By way of example, in this embodiment, the affinity binding element can be an aptamer or a protein that exhibits specific binding to a SARS-CoV-2 protein (e.g., the S protein of the SARS-CoV-2 virus). By way of example, similar to the previous embodiment, the affinity binding element can be the ACE2 enzyme, which exhibits specific binding to the SARS-CoV-2 S protein.

The SERS module can further include a laser source 1004 that can provide radiation for exciting one or more Raman active transitions of either the affinity binding element and/or the respective antigen. For example, as discussed above, in some embodiments in which the SERS surface 1002 is functionalized with ACE2 enzyme, the laser source (which can be, for example, in the form of a laser diode) can provide excitation radiation in a range of about 700 nm to about 1400 nm. In this embodiment, the laser radiation is directed via one or more optics 1007 onto the functionalized SERS surface and the Raman scattered radiation can be detected via a detector 1003. In this embodiment, one or more optics 1009 are disposed in front of the detector for focusing the Raman-scattered radiation onto the detector. The detector generates detection signal(s) in response to the detection of the Raman-scattered radiation, which are received by an analyzer 1005 that is in communication with the detector 1003 to receive the detection signal(s) generated by the detector.

The analyzer 1005 is configured to process the received Raman-scattered detection signals to identify and analyze the Stokes and/or anti-Stokes Raman peaks to determine whether the detected Raman signal indicates the presence of the target analyte in a sample under investigation. In this embodiment, a controller 1010 controls the operation of the laser and detector. For example, among other functions, it can provide triggers for activation of the laser and the detector.

The use of both electrochemical as well as Raman data can increase the reliability of a sensor according to such embodiments, and lower the rate of false positive signals. For example, the use of different detection modalities (i.e., electrochemical and optical) can help enhance the sensor's reliability by providing data in at least two detection channels that rely on different physical/chemical processes for the detection of an analyte (e.g., a pathogen) of interest.

Air Monitoring System

In another aspect, an air monitoring system is disclosed. With reference to FIGS. 11-16, such an air monitoring system 1100 according to an embodiment of the present teachings for monitoring ambient air, e.g., to detect one or more pathogens and/or other target contaminants includes a plurality of ports 112a, 112b, and 112c (herein collectively referred to as ports or inlet ports, or inlets 112) through which samples of ambient air can be introduced via their respective conduits 114a, 114b, and 114c, into a particle collection module 116, which includes a housing 116a that provides an enclosure for receiving samples of the ambient air via the inlet ports 112.

A plurality of filters 118a, 118b, and 118c (herein collectively referred to as filters 118) can be disposed at or in proximity of each of the ports 112 (e.g., in the conduit associated with each of the ports) to filter the sampled air entering the respective conduit, e.g., to remove dust particles or other contaminants. In some embodiments, the filters 118 can be a 2-micron filter. Some examples of suitable filters that are commercially available can include, without limitation, include those marketed by Whatman or Air Filters, Inc, U.S.A.

In this embodiment, an impeller, such as a fan 120, can be placed in proximity of each of the ports 112, e.g., in the conduit connecting the port to the collection housing 116, for facilitating the introduction of samples of the ambient air into the respective port.

A plurality of sensors 1 and 2 are disposed around the perimeter of the air-collection housing 116. Although in this embodiment only two sensors are depicted, in other embodiments one, or more than two, sensors may be employed. As discussed in more detail below, the sensors can be actuated at different times, e.g., in accordance with a predefined temporal schedule, to receive samples of the air collected in the air collection housing 116 and analyze the received air samples for the presence of one or more target particles (e.g., viral particles) of interest. Without any loss of generality, in the following discussion the target particles of interest are assumed to be viral particles, but it should be understood that the present teachings can be employed to detect other types of particles, including other types of pathogens (e.g., bacteria) in environmental samples.

In this embodiment, the sensors 1 and 2 are implemented in an identical manner. Hence, without any loss of generality, the structure of only the sensor 1 is described in detail below. Those having ordinary skill in the art will appreciate that the other sensors can have a similar structure.

The sensor 1 is removably connected to the air collection housing using any suitable mechanical coupling mechanisms, such as brackets, bayonet coupling, etc. As discussed in more detail below, in some embodiments, a plurality of sensors are disposed within a cartridge that can be coupled to the air collection housing.

An electromagnetically-actuable valve 1200 separates the sensor 1 from the inner space of the air collection housing. As discussed in more detail below, once actuated, the valve 1200 opens to allow a sample of the air collected within the air collection housing 116 to be introduced into the sensor 1.

The sensor 1 includes a nozzle 1202 through which the air sample can be accelerated to be incident on a porous impaction material 1204. By way of example, the impaction material can be formed of porous polyurethane foam.

As discussed in more detail below, the impaction material 1204 can separate one or more target pathogens (e.g., one or more viruses), if present in the sampled incoming air, from other particulates. By way of example, the impaction material 1204 can be configured to substantially absorb particles having a size greater than about 1 micron, but allow passage of particles with a size greater than about 1 micron around it.

In some embodiments, the efficiency of separating the pathogens (or other analytes of interest) using the impaction material 1204 can be at least about 60%, or at least about 70%, or at least about 80%, or at least about 90%, or at least about 95%.

By way of example, in some embodiments, the impaction materials disclosed in U.S. Pat. No. 6,435,043 (herein referred to as the '043 Patent), which is herein incorporated by reference in its entirety, can be employed in the practice of the present teachings. Briefly, the '043 Patent discloses inertial impactors that employ a porous material for collecting particulates in a gas, e.g., ambient air. The air can be drawn through an inlet onto the surface of an impaction substrate, which can collect particles having an inertia too great to be able to follow the curved path of the airstream. The impaction material can be a porous substrate, e.g., a polyurethane foam with a density of 0.019 or 0.031 g/cm. The remaining particles (e.g., the target viral particles) that do not have sufficient energy to be absorbed by the impaction material pass around the impaction material.

The sensor 1 further includes a capture filter 1206, which is placed in a well 1208 and can capture at least a portion of the particles passing around the impaction material. In addition to holding the capture filter, the well 1208 can also function as a container for receiving a buffer stored in a reservoir 1210 (herein referred to as "the capture buffer") when a valve 1211 separating the reservoir 1210 from the well 1208 is actuated to allow the buffer to exit the reservoir and come into contact with the a capture filter 1206. The buffer (herein also referred to as "transport buffer") can recover the particles captured in the filter (capture filter), thereby releasing the particles of interest (e.g., viral particles), if any. Examples of filters include Whatman filter membranes of 0.1 mm as an example. The transport buffer could be Phosphate Buffered Salin (PBS) or Hank's balanced salt solution (HBSS).

More specifically, in use, the valve 1200 can be opened to allow the introduction of a sample of the air collected in the air-collection housing 116 into the sensor 1. As discussed above, the capture filter can capture at least a portion of target particles (e.g., viral particles), when present in the sampled air. After the passage of a preselected time interval, the valve 1200 can be closed and the valve 1211 can be opened to allow the flow of the capture buffer stored in the reservoir 1210 into the well 1208.

The transport buffer can release at least a portion of the particles (e.g., particles containing a target virus) from the filter 1206, thereby forming a mixture of the released particles and the buffer.

In some embodiments, an electromagnetically-actuable mixer 1212 can be placed in the well 1208 so as to mix the capture buffer and the particles released from the capture filter into the buffer. In some embodiments, the mixer can be actuated substantially concurrently with the actuation of the valve 1211. In other embodiments, the mixer can be actuated after a predefined temporal interval after the actuation of the valve 1211.

An electromagnetically-actuable valve 1214 coupled to the well can be actuated to introduce the mixture of the buffer and the particles of interest, if present in the air sample, into a conduit 1216 that leads to two reservoirs 1218 and 1220, one of which stores reagents for facilitating the detection of one or more genetic components of the viral particles of interest. By way of example, such a reagent can be guanidine isothiocyanate (e.g., 2M final concentration) The other reservoir stores one or more reagents suitable for processing the viral particles to facilitate the detection of one or more viral proteins, for example (1) sodium dodecyl sulphate (SDS) at a final concentration of 0.2%; (2) a final concentration of 0.1%-1% Triton X-100, or (3) 0.1% Tween 20.

The actuation of the valve 1214 can be performed after a predefined time interval subsequent to the activation of the valve 1211. For example, this time interval can be selected to ensure that the vial particles, if captured by the capture filter, are released from the filter into the buffer and sufficient mixing of the buffer and the released viral particles is achieved, e.g., via an electromagnetically-actuable mixer. For example, in some embodiments, the valve 1214 can be actuated after a time interval in a range of about 1 minute to about 10 minutes, though other time intervals can also be employed.

The conduit 1216 includes a central portion 1216a that receives the buffer containing the released particles and leads to two branches 1216b/11216c, where the branch 1216b leads to the reservoir 1218 in which one or more reagents suitable for lysis and extraction of viral genetic components (e.g., viral RNA) is stored (herein also referred to as "RNA processing reagent") and the branch 1216c leads to the reservoir 1220 in which one or more reagents for stabilizing viral proteins and facilitating their detection is stored (herein referred to as "protein processing reagent"). In many embodiments, the RNA processing reagent contains guanidine as a component while the protein processing reagent lacks guanidine. Some examples of suitable RNA and protein reagents are those that were described above in connection with the previous embodiments.

The reservoirs 1218 and 1220 include two inlet valves 1218a/1220a, which can be actuated concurrently with the actuation of the valve 1214 (or a short time (e.g., a few seconds) after the actuation of the valve 1214) to allow the mixture of the capture buffer and the associated viral particles, if any, to be introduced into RNA and protein reagents. Subsequent to a predefined time interval, two outlet valves 1218b/1220b of the reservoirs 1218 and 1220 can be actuated to allow the sample processed by the RNA/DNA reagent(s) and the protein reagent(s) to be introduced into two sensing units 1222 and 1223 of the sensor 1. The sensing unit 1222 is configured to detect one or more target genetic components (e.g., RNA segments) of the virus of interest and the sensing unit 1223 is configured to detect one or more target viral proteins.

The sensing units 1222 and 1223 can be implemented in a manner discussed above as electrochemical sensors that are functionalized with aptamers and/or oligonucleotides that exhibit specific binding to protein(s) and/or genetic components (e.g., RNA segments) of interest. In some embodiments, instead of or in addition to the aptamers and/or oligonucleotides, the electrochemical sensors can be functionalized with synthetic recognition elements formed as synthetic polymers coupled to carbon nanotubes, e.g., in a manner discussed above.

Further, in some embodiments, one or both sensing units 1222 and 1223 can include a plurality of sensing modules (such as sensing modules 1222a, 1222b, . . . , and 1222n and sensing modules 1223a, 1223b, . . . , and 1223n) for detecting different proteins and/or different genetic components (e.g., different RNA segments) of a virus. In other words, each sensing unit can be designed to provide a multiplexed detection capability, e.g., to increase the detection selectivity and/or sensitivity.

The sensing modules of each sensor can generate one or more electrical signal(s) in response to interaction of the sample with the sensing module. A potentiostat 1225 can measure the electrical signal generated by each of the sensing modules. More particularly, in this embodiment, the potentiostat 1225 is coupled to the sensing modules via a multiplexer, which operates under the control of a microcontroller 1227, to connect the potentiostat to the sensing modules, one at a time (i.e., in a serial fashion).

The potentiostat can measure the electrical signal(s) generated by the sensing modules, e.g., due to a change in impedance of a functionalized electrode, in response to exposure to the sampled air.

The microcontroller 1227 can also be in communication with the potentiostat 1225 to receive the measured signals generated by the potentiostat and process the received signals to determine whether a sensing module has detected the presence of a target viral particle in an air sample.

In particular, the microcontroller 1227 can be programmed to process the received signals according to a predefined protocol. For example, the amplitude of an electrical signal generated by a sensing module can be compared with a predefined threshold to determine whether the electrical signal generated by that sensing module indicates the detection of a viral genetic component or protein by the sensing unit. By way of example, when the amplitude of the electrical signal exceeds the threshold, the microcontroller can indicate the detection of a viral particles of interest.

In this embodiment, the system 1100 includes an alarm system 1300, which is in communication with, and operates under the control of, the microcontroller 1217 to generate an alarm (e.g., an audible and/or a visual alarm) when the microcontroller determines the presence of a target virus in the sampled air. The alarm system 1300 can be implemented in a variety of known ways in the art.

The microcontroller can also be programmed to actuate the various valves of the system, e.g., in a manner discussed above. By way of example, in some embodiments, the microcontroller 1227 can be in communication with one or more electromagnetic relays 1301, which are in turn in communication with the valves. The microcontroller can activate one or more relays associated with a sensor so as to actuate one or more valves of the sensor, e.g., in a manner discussed above.

The microcontroller 1227 can also be programmed to actuate different sensors (e.g., sensors 1 and 2) at different times according to a predefined temporal schedule, e.g., every hour. By way of example, in some embodiments, the system 1100 can include 24 sensors and the microcontroller can be programmed to actuate the sensors in series on an hourly basis to collect and analyze different samples of the ambient air during different hourly intervals in a 24-hour time period. It should be understood that any suitable number of sensors can be employed in a system according to the present teachings, e.g., based on a particular application.

In some embodiments, the microcontroller can send a signal after a predefined time interval, and/or once the last sensor has been actuated and the signal from that sensor has been collected, to a remote server to alert an operator that the sensors need to be replaced. For example, in embodiments in which 24 sensors are employed for hourly testing of the ambient air, the microcontroller can send a replacement signal every 24 hours.

In some embodiments, the sensors are placed in a cartridge that can be easily coupled to the air collection housing and be removed from the housing for replacement with another cartridge.

By way of example, FIG. 16 schematically depicts another embodiment of a system 2000 according to the present teachings, which includes an air collection housing 2002 having a parallelepiped shape. A cartridge 2004 carrying a plurality of sensors 2006 according to the present teachings can be removably coupled to the air collection housing 2002 to be in fluid communication with the air collected in the air collection housing upon actuation of a valve separating the sensor from the air collection housing, e.g., in a manner discussed above.

A variety of mechanisms can be employed for coupling the cartridge to the air collection housing. By way of example, in this embodiment, the cartridge housing includes a plurality of slide rails 2008 that can be removably inserted into a plurality of slots 2010 provided on a side surface of the air collection housing.

Referring again to FIG. 11, the system 100 can also include a communications module 1400 that operates under the control of the controller 1217 and can communicate test results and/or various signals (e.g., a cartridge replacement signal) to a remote server, e.g., for alerting an operator, for storage and/or additional processing.

In some embodiments, various components of the system 1100 can be integrated within a single housing, which can be formed of a variety of suitable materials. By way of example, the housing can be formed of a variety of polymeric materials, e.g., PDMS. In other embodiments, one or more components of the system 1100 can be disposed in one housing and the other components of the device can be disposed in another housing. For example, in some embodiments, the processing of the electrical signals generated by the sensors can be performed on a remote server, which receives the signals and processes those signals in accordance with a predefined protocol.

In some embodiments, the system 1100 can be configured for the detection of SARS-COV-2 virus in environmental samples. As noted above, coronavirus disease 2019 (COVID-19), caused by the virus, Acute Respiratory Syndrome Coronavirus 2 (SARS-CoV-2), is effectively transmitted by droplets, aerosols, and contact with contaminated surfaces. In some embodiments, a system according to the present teachings can allow rapid, on-site detection of relevant SARS-CoV-2 biomarkers at low (nM-pM) concentrations.

For example, in some embodiments, the sensors of a system 1100 according to the present teachings can be configured to detect multiple SARS-CoV-2 specific nucleic acid sequences based on N, S, E, and ORF lab genes and structural proteins including Spike and Nucleocapsid proteins. As discussed in detail above, the detection of both viral genetic components as well as viral proteins can enhance the selectivity and sensitivity for detection of SARS-CoV-2. For example, in some embodiments, a system according to the present teachings can detect SARS-CoV-2 virus in air samples with sensitivity of less than 1 viral particle/liter and selectivity for detection of SARS-CoV-2 but no other coronaviruses.

The systems, sensors, and methods according to the present teachings provide a number of advantages. For example, they allow detection of pathogens, and in particular SARS-CoV-2 virus, in biological specimens in an easy and rapid way. Further, they allow such detection without a need to label the pathogens, e.g., via fluorescent labeling. In addition, the detection of both protein(s) and genetic material(s) associated with a pathogen as taught herein enhanced the reliability of the test. Further, it allows the detection of emergent pathogens in a family.

Those having ordinary skill in the art will appreciate that various changes can be made to the above embodiments without departing from the scope of the invention.

What is claimed is:

1. A system for detecting at least one protein and at least one genetic component associated with at least one pathogen of a biological specimen, comprising:
    a disposable cartridge frame comprising:
        a sample inlet port configured to receive the biological specimen;
        a first reservoir containing a protein buffer for preparing a sample of the biological specimen for detection of a target protein associated with the at least one pathogen in the biological specimen;
        a second reservoir containing a genetic buffer for preparing the sample of the biological specimen for detection of a target genetic component associated with the at least one pathogen in the biological specimen, wherein at least one reagent of one of the protein and the genetic buffer is absent from the other buffer,
        a first sensor configured to detect the target protein associated with the at least one pathogen in the sample;
        a second sensor configured to detect the target genetic component associated with the at least one pathogen in the sample; and
        at least one release mechanism coupled to the first and the second reservoirs for releasing at least a portion of a liquid in the first reservoir for transfer to the first sensor and for releasing at least a portion of a liquid in the second reservoir for transfer to the second sensor.

2. The system of claim 1, wherein the first sensor comprises a working electrode functionalized with a first affinity binding element exhibiting specific binding to the target protein and wherein the second sensor comprises a working electrode functionalized with a second affinity binding element exhibiting specific bind to the target genetic component.

3. The system of claim 1, wherein the first sensor comprises a first plurality of sensing units for detecting a plurality of different target proteins associated with the at least one pathogen such that each of the first plurality of the sensing units is configured to detect a different one of the plurality of different target proteins.

4. The system of claim 3, wherein the second sensor comprises a second plurality of sensing units for detecting a plurality of different target genetic components associated with the at least one pathogen such that each of the second plurality of the sensing units is configured to detect a different one of the plurality of genetic components.

5. The system of claim 4, wherein the first plurality of sensing units comprises a plurality of electrochemical sensors each functionalized with a different affinity binding element such that each of the affinity binding elements exhibits specific binding to one of the different target proteins.

6. The system of claim 1, wherein the biological specimen comprises any of a liquid biopsy specimen, a breath sample, an air sample and a waste water sample.

7. The system of claim 1, further comprising a first sample-transfer fluidic channel extending from the sample inlet port to an inlet port of the first reservoir for transferring at least a first portion of the biological specimen to the first reservoir, wherein an interaction of the first portion of the biological specimen with the protein buffer generates a first processed sample.

8. The system of claim 7, further comprising a first sample-delivery fluidic channel for transferring the first processed sample to the first sensor and a second sample-transfer fluidic channel configured to deliver at least a second portion of the biological specimen to an inlet port of the second reservoir, wherein an interaction of the second portion of the biological specimen with the genetic buffer generates a second processed sample.

9. The system of claim 8, further comprising an amplification well in fluid communication with the second reservoir for receiving the second processed sample released from the second reservoir, wherein the amplification well comprises one or more reagents required for amplification of the target genetic component for generating an amplified sample.

10. The system of claim 9, further comprising a second sample-delivery fluidic channel for delivering the amplified sample to the second sensor.

11. The system of claim 9, further comprising at least one of a heating and a heating and cooling device thermally coupled to the amplification well.

12. The system of claim 1, wherein each of the first and second sensors comprises any of an electrochemical sensor, and an optical sensor.

13. The system of claim 12, wherein each of the first and second sensor comprises an electrochemical sensor.

14. The system of claim 2, wherein the first affinity binding element comprises any of an antibody, an aptamer, a SOMAmer, a raptomer, and a megastar.

15. The system of claim 14, wherein the second affinity binding element comprises an oligonucleotide having a complementary oligonucleotide sequence relative to the target genetic component.

16. The system of claim 15, wherein the target genetic component comprises any of a DNA and an RNA segment.

17. The system of claim 1, wherein the biological specimen comprises a biopsy liquid.

18. The system of claim 1, wherein the at least one pathogen comprises at least one of a virus and a bacterium.

19. The system of claim 18, wherein the virus comprises any of SARS-CoV-2, Influenza A and B viruses, a Corona virus, a Zika virus, Ebola, a Rift Valley fever virus.

20. The system of claim 18, wherein the bacterium comprises any of *Yersinia pestis*, Methicillin Resistant *Staphylococcus Aureus* (MRSA).

21. The system of claim 1, further comprising an analysis module in communication with the first and second sensor for receiving signals generated thereby and processing the signals to determine whether the at least one pathogen is present in the biological specimen.

22. The system of claim 4, wherein the second plurality of sensing units comprises a plurality of electrochemical sensors each functionalized with a different affinity-binding element such that each of the affinity binding elements exhibits specific binding to each one of the plurality of the different target genetic components.

23. The system of claim 22, wherein the affinity binding elements comprise any of an antibody, an aptamer, a SOMAmer, a nanobody, a monobody, a megastar or combinations thereof.

24. The system of claim 23, wherein the affinity binding elements comprise a plurality of oligonucleotide each having a nucleotide sequence complementary to a nucleotide sequency of one the genetic components.

25. The system of claim 1, further comprising at least one transparent window positioned relative to one of the first and second sensor to allow optical access to the sensor.

26. The system of claim 1, wherein the first sensor and the second sensor includes a housing comprising a polymer.

27. The system of claim 26, wherein the polymer comprises any of PDMS and polyurethane.

28. The system of claim 1, wherein the at least one pathogen comprises a plurality of pathogens and at least one of the first and second sensor comprises a plurality of sensing units configured to detect different proteins or genetic components associated with the different pathogens.

29. A disposable cartridge for use in a point-of-care (POC) system for detecting at least one protein and at least one genetic component associated with a pathogen in a biological specimen, comprising:
　a cartridge frame, comprising:
　　a sample-receiving well for receiving the biological specimen,
　　a first reservoir containing a protein buffer for preparing the sample for detection of the target protein,
　　a second reservoir containing a genetic buffer for preparing the sample for detection of the genetic component, wherein at least one reagent of one of the protein and genetic buffers is absent from the other buffer,
　　a first sample-processing well in fluid communication with the sample-receiving well and the first reservoir for receiving a first portion of the sample and at least a portion of the protein buffer, wherein an interaction of the sample and the protein buffer generates a first processed sample,
　　a second sample-processing well in fluid communication with the sample-receiving well and the second reservoir for receiving a second portion of the sample and at least a portion of the genetic buffer, wherein an interaction of the second portion of the sample with the genetic buffer generates a second processed sample, a first sensor in fluid communication with the first sample-processing well for receiving the first processed sample for detecting the target protein associated with the pathogen, and a second sensor in fluid communication with the second sample-processing well for receiving the second processed sample for detecting the target genetic component associated with the pathogen.

30. The system of claim 1, wherein the genetic buffer comprises at least one of tris-HCL (TE) buffer, PBS (potassium-buffered saline) or HBSS (Hank's balanced salt solution).

* * * * *